US012019961B2

United States Patent
Chen et al.

(10) Patent No.: US 12,019,961 B2
(45) Date of Patent: Jun. 25, 2024

(54) METHOD AND SYSTEM FOR DETERMINING TRANSPORTATION SAFETY OF PULVERIZED COAL

(71) Applicant: Northwestern Polytechnical University, Shaanxi (CN)

(72) Inventors: Fuzhen Chen, Shaanxi (CN); Hong Yan, Shaanxi (CN)

(73) Assignee: Northwestern Polytechnical University, Shaanxi (CN)

( * ) Notice: Subject to any disclaimer, the term of this patent is extended or adjusted under 35 U.S.C. 154(b) by 772 days.

(21) Appl. No.: 17/137,623

(22) Filed: Dec. 30, 2020

(65) Prior Publication Data
US 2022/0164499 A1    May 26, 2022

(30) Foreign Application Priority Data
Nov. 17, 2020  (CN) .......................... 202011284318.9

(51) Int. Cl.
  *G06F 30/25*   (2020.01)
  *G01N 33/22*   (2006.01)
  *G06F 111/10*  (2020.01)
(52) U.S. Cl.
  CPC .......... *G06F 30/25* (2020.01); *G01N 33/222* (2013.01); *G06F 2111/10* (2020.01)
(58) Field of Classification Search
  CPC .... G06F 30/25; G06F 2111/10; G01N 33/222
(Continued)

(56) References Cited

U.S. PATENT DOCUMENTS

| 4,244,529 A | * | 1/1981 | DeGabriele | ............. | B02C 23/04 |
| | | | | | 241/31 |
| 4,653,698 A | * | 3/1987 | Cooper | .................. | B02C 23/04 |
| | | | | | 241/31 |

(Continued)

FOREIGN PATENT DOCUMENTS

| CN | 106018204 A | * | 7/2021 | ............. G01N 15/00 |
| CN | 113177346 A | * | 7/2021 | ............. G01N 15/00 |
| JP | 5187612 B2  | * | 4/2013 | |

OTHER PUBLICATIONS

Wojciech P. Adamczyk (Application of the Numerical Techniques for Modelling Fluidization Process Within Industrial Scale Boilers, Arch Computat Methods Eng (2017) 24:669-702) (Year: 2017).*

(Continued)

*Primary Examiner* — Iftekhar A Khan
(74) *Attorney, Agent, or Firm* — Syncoda LLC; Feng Ma

(57) ABSTRACT

The present disclosure relates to a method and system for determining transportation safety of pulverized coal. The method includes: acquiring coal particle data during transportation of pulverized coal, where the coal particle data is size data of a coal particle accumulation; determining a particle model of the coal particle accumulation during the transportation of the pulverized coal according to the size data; establishing a constitutive theoretical model to describe all flow regimes of a coal granular medium; numerically discretizing the constitutive theoretical model by using a numerical method to obtain discrete equations; calculating a movement process of the coal granular medium according to the discrete equations and the particle model of the coal granular medium to obtain a calculation result; plotting the calculation result by using post-processing software Tecplot to obtain relevant information of a coal particle flow; and determining whether the pulverized coal transportation process is safe.

4 Claims, 5 Drawing Sheets

(58) Field of Classification Search
USPC .......................................................... 703/2
See application file for complete search history.

(56) References Cited

U.S. PATENT DOCUMENTS

| | | | |
|---|---|---|---|
| 9,267,831 B2* | 2/2016 | Fu | G01F 1/86 |
| 9,494,319 B2* | 11/2016 | Sutton | B02C 25/00 |
| 9,604,226 B2* | 3/2017 | Storm | B02C 23/04 |
| 2011/0032255 A1* | 2/2011 | Favier | G06F 30/23 |
| | | | 345/420 |
| 2012/0259602 A1* | 10/2012 | Nishiura | G06F 30/20 |
| | | | 703/6 |
| 2015/0213163 A1* | 7/2015 | Yang | G06F 30/20 |
| | | | 703/2 |

OTHER PUBLICATIONS

Jin et al. (Application of CPFD method in the simulation of vertical dense phase pneumatic conveying of pulverized coal, Powder Technology 357 (2019) 343-351) (Year: 2019).*

Lan et al. (Study on the migration of pulverized coal in CBM wellbore, Journal of Petroleum Science and Engineering 156 (2017) 740-747) (Year: 2017).*

* cited by examiner

Calculation results of the present disclosure

Experimental results

METHOD AND SYSTEM FOR DETERMINING TRANSPORTATION SAFETY OF PULVERIZED COAL

TECHNICAL FIELD

The present disclosure relates to the field of determination on transportation safety of pulverized coal, in particular to a method and system for determining transportation safety of pulverized coal.

BACKGROUND

During transportation, pulverized coal for firing boilers often slips, spreads and migrates away from the initial accumulation state because of external disturbances, such as vibrations and collisions of the transportation equipment, or the harsh conditions such as earthquakes, typhoons and rainfall. As the contact area of the pulverized coal with the outside air increases, the pulverized coal is prone to spontaneous combustion or even explosion. Meanwhile, the pulverized coal with large accumulation height and volume will cause impact and damage to the surrounding objects during the slipping process, and some pulverized coal particles will rise into the air, causing air pollution. All of these have caused great safety risks to the external environment. Therefore, there is an urgent need for a method and system for determining the transportation safety of pulverized coal.

SUMMARY

The present disclosure aims to provide a method and system for determining transportation safety of pulverized coal. The present disclosure can quickly and accurately determine whether the coal particles will slip and determine the spreading range after the slip.

To achieve the above objective, the present disclosure provides the following solutions:

A method for determining transportation safety of pulverized coal, including:
  acquiring coal particle data during transportation of pulverized coal, where the coal particle data is the size data of a coal particle accumulation, including length data, width data and height data of the coal particle accumulation;
  determining a particle model of the coal particle accumulation during the transportation of the pulverized coal according to the size data;
  establishing a constitutive theoretical model to describe all flow regimes of a coal granular medium, where the all flow regimes of the coal granular medium include solid-like, liquid-like, gas-like and inertial regimes;
  numerically discretizing the constitutive theoretical model by using a numerical method to obtain discrete equations;
  calculating a movement process of the coal granular medium according to the discrete equations and the particle model of the coal granular medium to obtain a calculation result, where the calculation result includes a field variable and a displacement;
  plotting the calculation result by using post-processing software Tecplot to obtain relevant information of a coal particle flow, where the relevant information includes a spatial distribution, a velocity field distribution, a spreading range and accumulation height information of the coal particle flow; and
  determining whether the pulverized coal transportation process is safe according to the relevant information of the coal particle flow.

Optionally, the determining a particle model of the coal particle accumulation during the transportation of the pulverized coal according to the size data specifically includes:
  determining a three-dimensional (3D) geometric model of the coal particle accumulation during the transportation of the pulverized coal according to the size data; and
  meshing the 3D geometric model by using meshing software to obtain a particle model.

Optionally, the establishing a constitutive theoretical model to describe all flow regimes of a coal granular medium specifically includes:
  defining solid-like and liquid-like particles as a dense coal particle flow, gas-like particles as a sparse coal particle flow and inertial particles as an ultra-sparse coal particle flow according to different levels of sparseness;
  establishing a theoretical model to describe a dense coal particle flow region, a theoretical model to describe a sparse coal particle flow region and a theoretical model to describe an ultra-sparse coal particle flow region respectively; and
  establishing a principle of transformation between the dense coal particle flow and the sparse coal particle flow and a principle of transformation between the sparse coal particle flow and the ultra-sparse coal particle flow respectively.

Optionally, the calculating a movement process of the coal granular medium according to the discrete equations and the particle model of the coal granular medium to obtain a calculation result specifically includes:
  setting an initial velocity of the coal granular medium to 0 and an initial pseudo-temperature to 0, and determining an initial position of the coal granular medium according to the particle model of the coal granular medium;
  calculating a variation of the field variable per unit time and a variation of the displacement per unit time at each time step starting from moment 0 by the discrete equations; and
  performing leapfrog time update according to the variation of the field variable per unit time and the variation of the displacement per unit time to determine the field variable and displacement at all moments.

Optionally, the determining whether the pulverized coal transportation process is safe according to the relevant information of the coal particle flow specifically includes:
  obtaining historical data on slippage of the pulverized coal;
  obtaining a threshold of safety-related parameters of the pulverized coal transportation process according to the historical data on slippage of the pulverized coal, where the safety-related parameters of the pulverized coal transportation process include the spatial distribution, the velocity field distribution, the spreading range and the accumulation height information of the coal particle flow;
  determining whether the spatial distribution, the velocity field distribution, the spreading range and the accumulation height information of the coal particle flow are greater than the respective threshold;
  determining that the pulverized coal transportation process is not safe if the safety-related parameters of the pulverized coal transportation process are greater than the respective threshold; and determining that the pulverized coal transportation process is safe if the safety-related parameters of the pulverized coal transportation process are not greater than the respective threshold.

A system for determining transportation safety of pulverized coal, including:

a coal particle data acquisition module, for acquiring coal particle data during the transportation of pulverized coal, where the coal particle data is the size data of a coal particle accumulation, including length data, width data and height data of the coal particle accumulation;

a particle model determination module, for determining a particle model of the coal granular medium during the transportation of the pulverized coal according to the size data;

a constitutive theoretical model establishment module, for establishing a constitutive theoretical model to describe all flow regimes of a coal granular medium, where the all flow regimes of the coal granular medium include solid-like, liquid-like, gas-like and inertial regimes;

a numerical discretization module, for numerically discretizing the constitutive theoretical model by using a numerical method to obtain discrete equations;

a coal granular medium movement process calculation module, for calculating a movement process of the coal granular medium according to the discrete equations and the particle model of the coal granular medium to obtain a calculation result, where the calculation result includes a field variable and a displacement;

a post-processing module, for plotting the calculation result by using post-processing software Tecplot to obtain relevant information of a coal particle flow, where the relevant information includes a spatial distribution, a velocity field distribution, a spreading range and accumulation height information of the coal particle flow; and a determining module, for determining whether the pulverized coal transportation process is safe according to the relevant information of the coal particle flow.

Optionally, the particle model determination module specifically includes:

a 3D geometric model establishment unit, for determining a 3D geometric model of the coal particle during the transportation of the pulverized coal according to the size data; and a meshing unit, for meshing the 3D geometric model by using meshing software to obtain a particle model.

Optionally, the constitutive theoretical model establishment module specifically includes:

a sparseness-based defining module, for defining solid-like and liquid-like particles as a dense coal particle flow, gas-like particles as a sparse coal particle flow and inertial particles as an ultra-sparse coal particle flow according to different levels of sparseness;

a theoretical model establishment unit, for establishing a theoretical model to describe a dense coal particle flow region, a theoretical model to describe a sparse coal particle flow region and a theoretical model to describe an ultra-sparse coal particle flow region respectively; and a transformation principle establishment unit, for establishing a principle of transformation between the dense coal particle flow and the sparse coal particle flow and a principle of transformation between the sparse coal particle flow and the ultra-sparse coal particle flow respectively.

Optionally, the coal granular medium movement process calculation module specifically includes:

an initial condition setting unit, for setting an initial velocity of the coal granular medium to 0 and an initial pseudo-temperature to 0, and determining an initial position of the coal granular medium according to the particle model of the coal granular medium;

a first determination unit, for calculating a variation of the field variable per unit time and a variation of the displacement per unit time at each time step starting from moment 0 by the discrete equations; and a second determination unit, for performing leapfrog time update according to the variation of the field variable per unit time and the variation of the displacement per unit time to determine the field variable and displacement at all moments.

According to specific embodiments of the present disclosure, the present disclosure has the following technical effects:

The present disclosure provides a method for determining transportation safety of pulverized coal. The determination method includes: acquiring coal particle data during transportation of pulverized coal, where the coal particle data is size data of a coal particle accumulation, including length data, width data and height data of the coal particle accumulation; determining a particle model of the coal particle accumulation during the transportation of the pulverized coal according to the size data; establishing a constitutive theoretical model to describe all flow regimes of a coal granular medium, where the all flow regimes of the coal granular medium include solid-like, liquid-like, gas-like and inertial regimes; numerically discretizing the constitutive theoretical model by using a numerical method to obtain discrete equations; calculating a movement process of the coal granular medium according to the discrete equations and the particle model of the coal granular medium to obtain a calculation result, where the calculation result includes a field variable and a displacement; plotting the calculation result by using post-processing software Tecplot to obtain relevant information of a coal particle flow, where the relevant information includes a spatial distribution, a velocity field distribution, a spreading range and accumulation height information of the coal particle flow; and determining whether the pulverized coal transportation process is safe according to the relevant information of the coal particle flow. The method of the present disclosure can quickly and accurately determine whether the coal particles will slip and determine the spreading range after the slip.

BRIEF DESCRIPTION OF DRAWINGS

To describe the technical solutions in the embodiments of the present disclosure or in the prior art more clearly, the following briefly describes the accompanying drawings required for describing the embodiments. Apparently, the accompanying drawings in the following description show merely some embodiments of the present disclosure, and a person of ordinary skill in the art may still derive other drawings from these accompanying drawings without creative efforts.

DETAILED DESCRIPTION

The following clearly and completely describes the technical solutions in the embodiments of the present disclosure with reference to the accompanying drawings in the embodiments of the present disclosure. Apparently, the described embodiments are merely a part rather than all of the embodiments of the present disclosure. All other embodiments obtained by a person of ordinary skill in the art based on the embodiments of the present disclosure without creative efforts should fall within the protection scope of the present disclosure.

An objective of the present disclosure is to provide a method and system for determining transportation safety of pulverized coal. The present disclosure can quickly and accurately determine whether the coal particles will slip and determine the spreading range after the slip.

To make the above objective, features and advantages of the present disclosure clearer and more comprehensible, the present disclosure is further described in detail below with reference to the accompanying drawings and specific embodiments.

Figure 1:
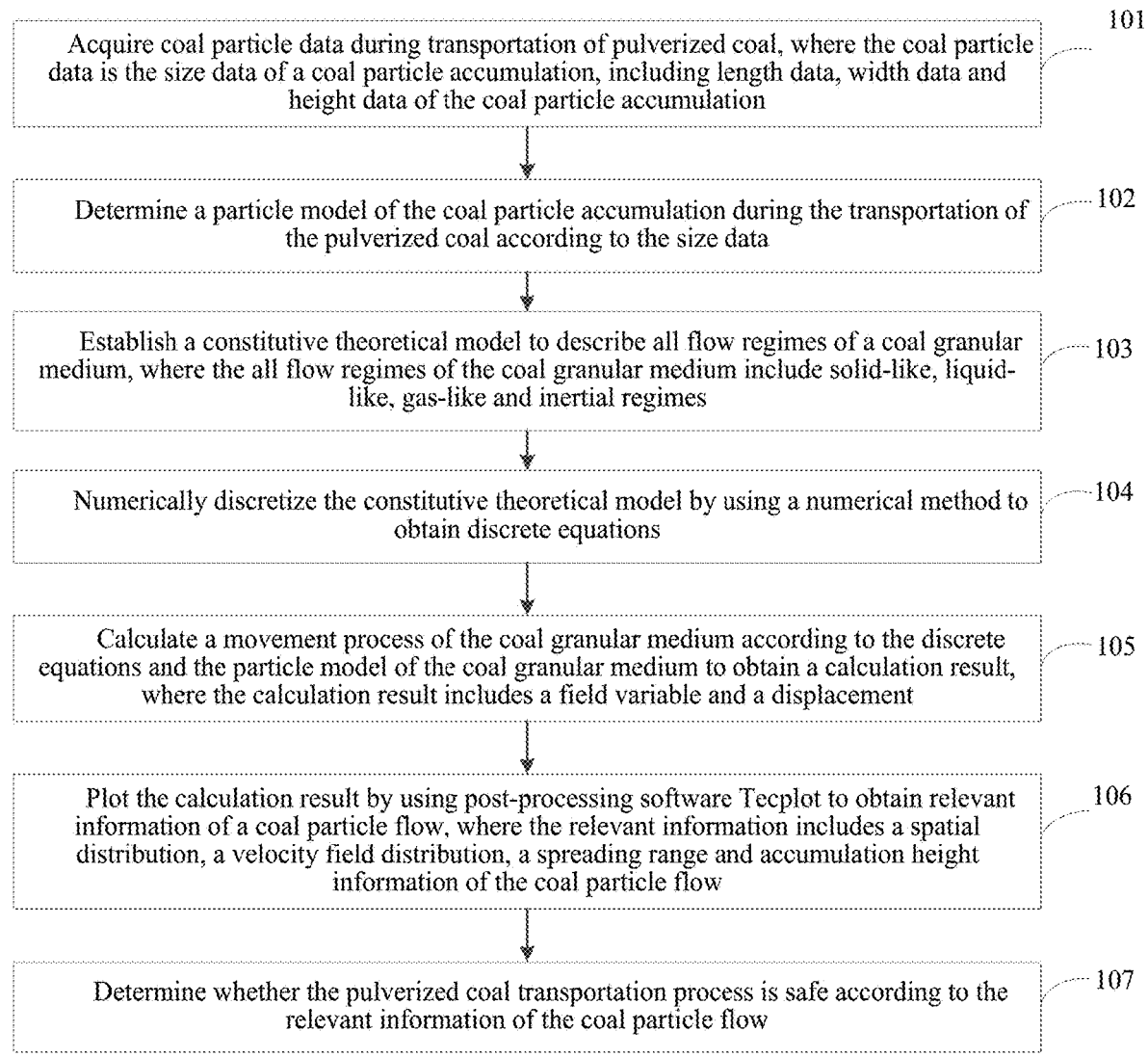
FIG. 1 is a flowchart of a method for determining transportation safety of pulverized coal according to the present disclosure.

The traditional description of the coal granular medium mostly stays in a single flow regime, which is quite far from the actual coal granular medium existing in and frequently transforming between multiple flow regimes in nature and industry. Only a few studies have derived the theories of multiple flow regimes based on the existing theories of single flow regimes. These theories use a numerical method for simulation, but they have complex and large amounts of calculations due to the need for equation iteration. Meanwhile, the multi-flow-regime theories only combine multiple but not all flow regimes of the coal granular medium, and the transitional connection between regimes is not yet mature. In order to solve these deficiencies, the present disclosure creatively proposes new theories to describe the solid-like, liquid-like, gas-like and inertial flow regimes of the coal granular medium. The transition between the regimes is smoother without equation iteration, and strictly follows the conservation of mass, momentum and energy. The existing multi-flow-regime calculations of the coal granular medium use a material point method (MPM) for discrete solution. The calculation process requires a background mesh, and the solving of the momentum equation relies on the background mesh. There are inevitably the defects of re-meshing, large-scale layout of the background mesh and repeated interpolation between the mesh and the material point. In addition, the MPM cannot simulate all the flow regimes of the coal granular medium. The present disclosure overcomes the deficiencies of the existing numerical methods, and can quickly and accurately determine whether the transportation of the pulverized coal is safe. The present disclosure adopts completely meshless particle methods, such as smoothed particle hydrodynamics (SPH), smoothed discrete particle hydrodynamics (SDPH) and discrete element method (DEM), which are suitable for different flow regimes of coal particles, ensuring accurate description and dynamic reproduction of each flow regime, and greatly reducing the calculation amount. The present disclosure provides a method for determining transportation safety of pulverized coal. As shown in FIG. 1, the determination method includes the following steps:

Step 101: Acquire coal particle data during transportation of pulverized coal, where the coal particle data is the size data of a coal particle accumulation, including length data, width data and height data of the coal particle accumulation.

Step 102: Determine a particle model of the coal particle accumulation during the transportation of the pulverized coal according to the size data. Specifically:

Determine a three-dimensional (3D) geometric model of the coal particle accumulation during the transportation of the pulverized coal according to the size data.

Mesh the 3D geometric model by using meshing software to obtain a particle model.

The 3D geometric model of the coal particle accumulation is established by commercial software, and imported into the meshing software to perform fine and uniform meshing. Finally, mesh files are imported into a program, and all are transformed into particles according to the principle of transforming one mesh into one particle. The specific process is:

1) Establish a geometric model of an actual coal granular medium material and a geometric model of the environmental conditions of the coal granular medium material by using 3D computer-aided design (CAD) software developed by SolidWorks, a subsidiary of France's Dassault Systemes.

2) Mesh the geometric model established in step 1) by Hypermesh software, a powerful computer-aided education (CAE) application software package.

Figure 2:
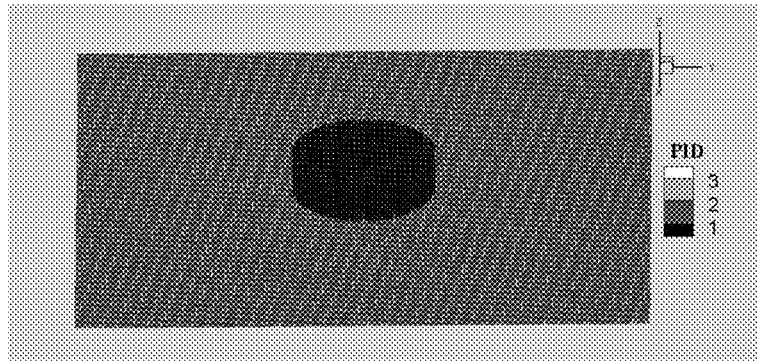
FIG. 2 shows a particle model of a coal particle cylinder collapsed on a free surface.

3) Import mesh files generated in step 2) into a self-compiled program to transform the meshes into particles, that is, according to the principle that one mesh corresponds to one particle, calculate the volume of a hexahedral mesh as the volume of an SPH particle by using an arbitrary hexahedron volume calculation method, and calculate the center of mass of the hexahedral mesh as the center of mass (initial position) of the SPH particle by using an arbitrary hexahedron center of mass calculation method, to obtain a particle model of the structure. As the core calculation data of the algorithm, the volume of a single SPH particle determines the mass of the single SPH particle, which will be involved in the following step (5). The center of mass of the SPH particle, which is the initial position of the SPH particle, directly determines the initial position of the matter. FIG. 2 shows a particle model of a coal particle cylinder collapsed on a free surface. In the figure, the darker-colored particles represent the particle cylinder in an initial accumulation state, and the lighter-colored flat particles below represent the free surface, which provides a boundary condition for the collapse of the particle cylinder. The coal particle cylinder has a radius of 75 mm and a height of 41.25 mm The size of the bottom boundary is 300 mm×300 mm, and the height of the bottom boundary is the height of a layer of particles. In the whole structure, there are a total of 182,484 particles.

Figure 3:
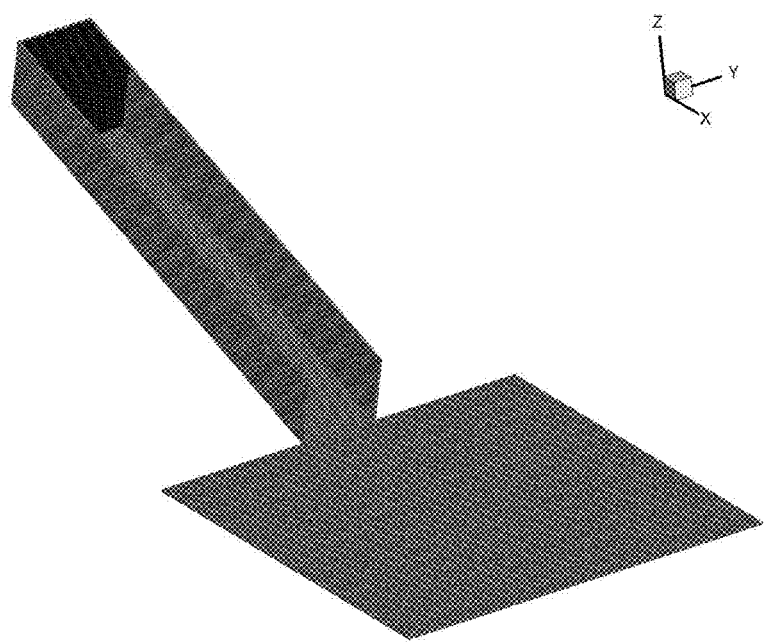
FIG. 3 shows a particle model of coal particles collapsing and slipping along a chute.

FIG. 3 shows a particle model of coal particles collapsing and slipping along a chute. In the figure, the darker-colored particles represent a coal particle accumulation initially at the top of the chute, and the lighter-colored particles below represent a boundary of the chute. The initial coal particle accumulation is 500 mm long, 500 mm high and 500 mm wide; the hypotenuse delimiting a boundary of the chute is 3,500 mm long, 500 mm high, and 500 mm wide; the lower plate is 3,000 mm long and 2,500 mm wide. In the whole structure, there are a total of 46,100 particles.

Figure 4:
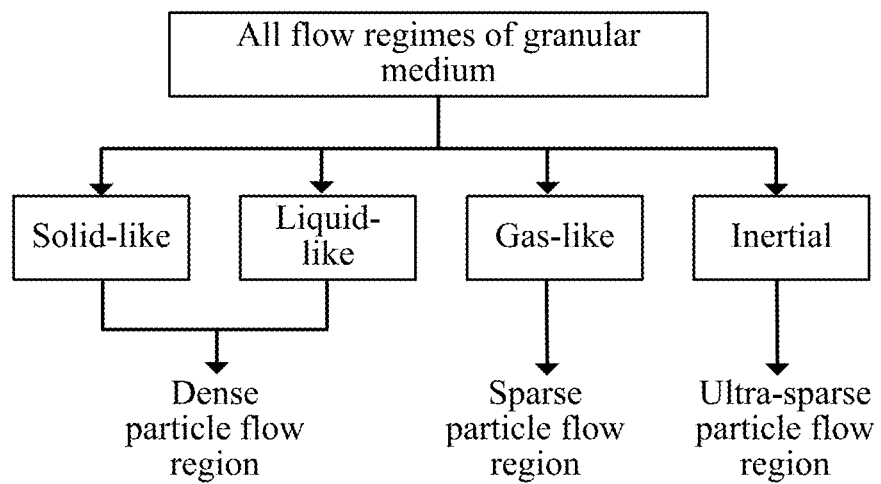
FIG. 4 shows all flow regimes of a coal granular medium divided based on different levels of sparseness.

Step 103: Establish a constitutive theoretical model to describe all flow regimes of a coal granular medium, where the all flow regimes of the coal granular medium include solid-like, liquid-like, gas-like and inertial regimes. Specifically:

Define solid-like and liquid-like particles as a dense coal particle flow, gas-like particles as a sparse coal particle flow and inertial particles as an ultra-sparse coal particle flow according to different levels of sparseness, as shown in FIG. 4.

Establish a theoretical model to describe a dense coal particle flow region, a theoretical model to describe a sparse coal particle flow region and a theoretical model to describe an ultra-sparse coal particle flow region respectively.

Figure 5:
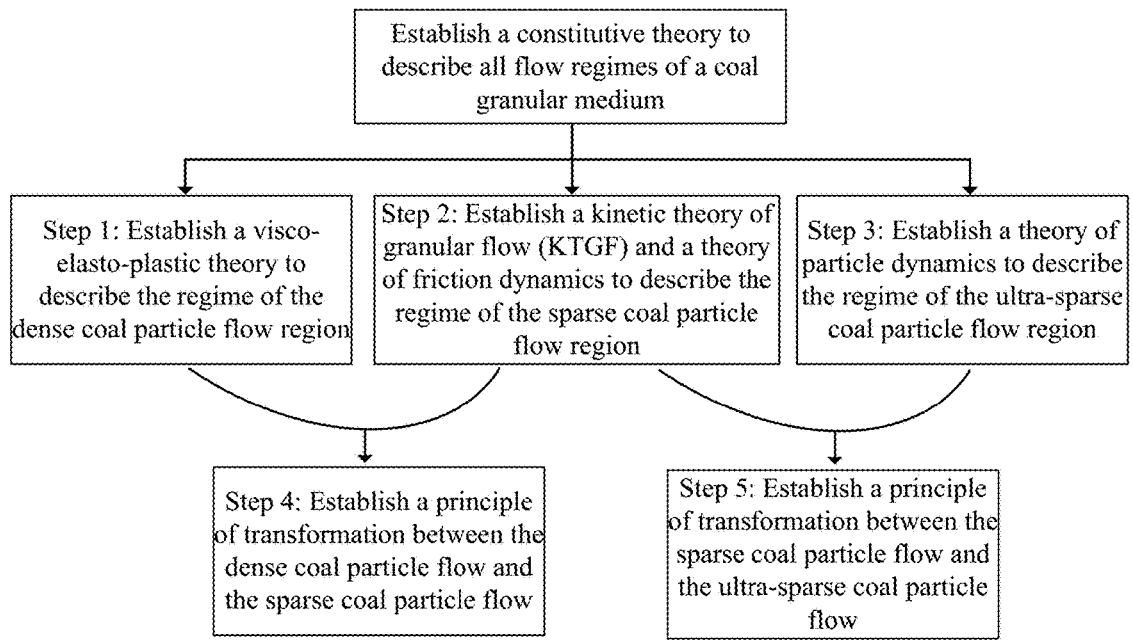
FIG. 5 shows a logical relationship between the steps of establishing an all-flow-regime constitutive theoretical model of the coal granular medium.

Establish a principle of transformation between the dense coal particle flow and the sparse coal particle flow and a principle of transformation between the sparse coal particle flow and the ultra-sparse coal particle flow respectively, as shown in FIG. 5.

As shown in FIG. 4, the coal granular medium has totally four flow regimes, including solid-like, liquid-like, gas-like and inertial regimes. According to different levels of sparseness, a solid-like and liquid-like region is defined as a dense coal particle flow region; a gas-like region is defined as a sparse coal particle flow region; an inertial regime region is defined as an ultra-sparse coal particle flow region. It is necessary to separately model all the flow regimes of the coal granular medium and establish the connection between the different regimes, which is the reason for the following steps. FIG. 5 shows a logical relationship between the steps of establishing an all-flow-regime constitutive theoretical model of the coal granular medium.

To establish the constitutive theory of all flow regimes of the coal granular medium, it is necessary to establish the constitutive theories of the three coal particle flow regions divided according to the four flow regimes of the coal granular medium, including a theory of the dense coal particle flow region, a theory of the sparse coal particle flow region and a theory of the ultra-sparse coal particle flow region. After the theories of these three flow regions are established, the principles of transformation between different regions are established respectively, including a transformation principle between the dense coal particle flow and the sparse coal particle flow and a transformation principle between the sparse coal particle flow and the ultra-sparse coal particle flow.

In Step 103, constitutive equations are derived from the constitutive theory, and the constitutive equations are discretized by using a numerical method to obtain discrete equations (Step 104). Thus, the program can be written and implemented on a computer.

Figure 6:
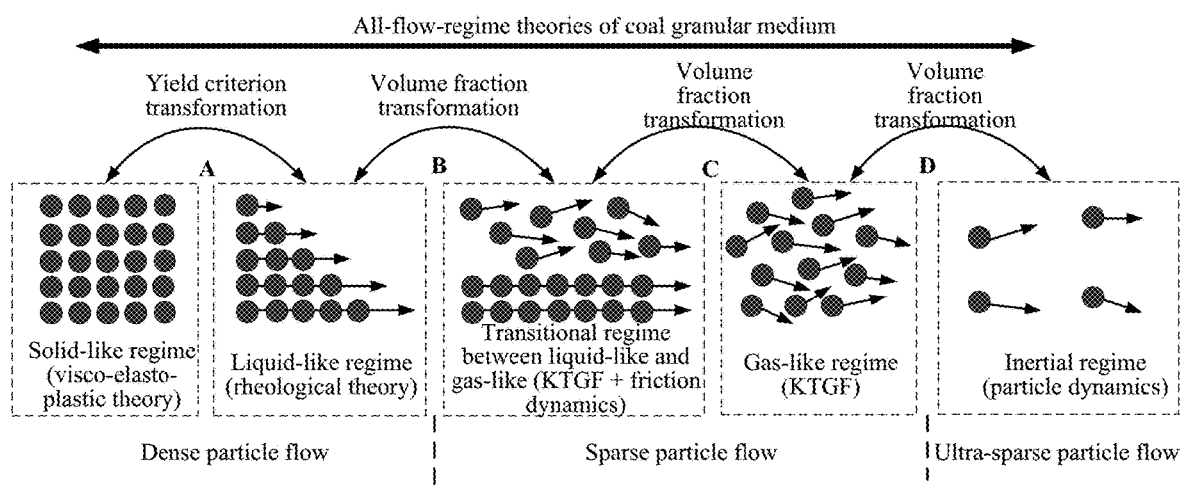
FIG. 6 shows all-flow-regime theories of the coal granular medium.

The all-flow-regime theory of the coal granular medium is shown in FIG. 6. The coal granular medium is divided into three large regions according to different flow regimes, namely a dense coal particle flow region ($0.5 \leq \xi_p \leq \xi_{max}$; $\xi_p$ represents a volume fraction of particles, $\xi_{max}$ represents the maximum volume fraction, the same below), a sparse coal particle flow region ($0.02 \leq \xi_p < 0.5$) and an ultra-sparse coal particle flow region ($\xi_p < 0.02$). In the dense coal particle flow region, the coal particle flow is in an incompressible regime, the particles are mainly in long-term contact, and the volume fraction of the particles remains basically unchanged. This region mainly includes solid-like and liquid-like regimes. In the sparse coal particle flow region, the coal particle flow is in a compressible regime, the volume fraction of the particles changes more obviously, and the two-body collisions are dominant between the particles. This region mainly includes a transitional regime between the liquid-like and gas-like regimes and the gas-like regime. In the ultra-sparse coal particle flow region, the characteristic time scale of the macroscopic flow of particles is significantly smaller than that of the microscopic collision, the two-body collision assumption between particles is no longer satisfied, and the macroscopic continuum description of particles is not followed. This region mainly includes the inertial regime of the particles.

Therefore, the constitutive theories adopted for different flow regimes of the coal granular medium are different:

a: The regime of the dense coal particle flow region is described by a visco-elasto-plastic constitutive theory. Specifically, the solid-like regime of the dense coal particle flow is described by an elasto-plastic theory, and the liquid-like regime of the dense coal particle flow is described by a rheological theory.

b: The regime of the sparse coal particle flow region is described by a kinetic theory of granular flow (KTGF) and a theory of friction dynamics. Specifically, the transitional regime between the liquid-like and gas-like regimes of the sparse coal particle flow is described by a combination of KTGF and friction dynamics, and the gas-like regime of the sparse coal particle flow is described by KTGF.

c: The regime of the ultra-sparse coal particle flow region is described by a theory of particle dynamics. Specifically, the inertial regime of the ultra-sparse coal particle flow is described by particle dynamics.

These different theories and the principles of transformation between them are illustrated below.

1) Visco-Elasto-Plastic Theory to Describe the Regime of the Dense Coal Particle Flow Region ($0.5 \leq \xi_p \leq \xi_{max}$)

First, dynamic control equations are established to describe the regime of the dense coal particle flow region:

$$\frac{d\rho}{dt} = -\frac{1}{\rho}\frac{\partial v^\alpha}{\partial x^\alpha} \tag{1a}$$

$$\frac{dv^\alpha}{dt} = \frac{1}{\rho}\frac{\partial \sigma^{\alpha\beta}}{\partial x^\beta} + f^\alpha \tag{1b}$$

$$\frac{dx_i^\alpha}{dt} = v_i^\alpha \tag{1c}$$

$\alpha$ and $\beta$ are free indexes, respectively representing directions x, y, z in space; $\rho$ represents an effective density of the coal granular medium, that is, an average density in space, $\rho = \rho_p \cdot \xi_p$; $\rho_p$ represents an actual density of the coal granular medium; $\xi_p$ represents the volume fraction of the coal granular medium; v represents a velocity of the coal granular medium; $\sigma^{\alpha,\beta}$ represents the total stress of the coal granular medium; $f^\alpha$ represents the other force, such as gravity and buoyant force in addition to the internal stress on the coal granular medium.

The total stress tensor $\sigma^{\alpha\beta}$ is expressed as the sum of an isotropic hydrostatic pressure and a stress deviator s:

$$\sigma^{\alpha\beta} = -p\delta^{\alpha\beta} + s^{\alpha\beta} \tag{2}$$

$\delta^{\alpha\beta}$ is a Kronecker function, $\delta^{\alpha\beta}=1$ when $\alpha=\beta$, and $\delta^{\alpha\beta}=0$ when $\alpha\neq\beta$.

The hydrostatic pressure p is expressed as a component of the total stress tensor:

$$p = -\frac{\sigma^{\gamma\gamma}}{3} = -\frac{1}{3}(\sigma^{xx} + \sigma^{yy} + \sigma^{zz}). \tag{3}$$

Therefore, the hydrostatic pressure and the stress deviator can be obtained by calculating the total stress tensor, and then the dynamic equations (1) can be solved.

The solving process of the total stress tensor $\sigma^{\alpha\beta}$ is explained below. First, the total strain rate is divided into an elastic strain rate and a plastic strain rate:

$$\dot{\varepsilon}^{\alpha\beta} = \dot{\varepsilon}_e^{\alpha\beta} + \dot{\varepsilon}_p^{\alpha\beta} \tag{1}$$

In the equation, $\varepsilon$ represents a strain; $\dot{\varepsilon}$ represents a strain rate; e represents the subscript of an elastic component; p represents the subscript of a plastic component. The total strain rate $\dot{\varepsilon}^{\alpha\beta}$ can be directly calculated by the equation.

$$\dot{\varepsilon}^{\alpha\beta} = \frac{1}{2}\left(\frac{\partial v^\alpha}{\partial x^\beta} + \frac{\partial v^\beta}{\partial x^\alpha}\right) \tag{2}$$

v represents the velocity of the particles. The coal granular medium is completely elastic before being plastic, following Hooke's law, and ignoring the quasi-static flow behavior.

$$\dot{\varepsilon}_e^{\alpha\beta} = \frac{\dot{s}^{\alpha\beta}}{2G} + \frac{1-2\upsilon}{3E}\dot{\sigma}^{\gamma\gamma}\delta^{\alpha\beta}. \tag{3}$$

$\dot{s}^{\alpha\beta}$ represents a deviator of a shear stress rate; $\upsilon$ represents a Poisson's ratio; E represents a Young's modulus; G represents a shear modulus.

$$G = \frac{E}{2(1+\upsilon)} \tag{4}$$

$\sigma$ represents a stress; $\dot{\sigma}$ represents a stress change rate; $\dot{\sigma}^{\gamma\gamma}$ represents the sum of three normal stress components, $\dot{\sigma}^{\gamma\gamma} = \dot{\sigma}^{xx} + \dot{\sigma}^{yy} + \dot{\sigma}^{zz}$. $\delta^{\alpha\beta}$ is a Kronecker function, $\delta^{\alpha\beta}=1$ when $\alpha=\beta$, and $\delta^{\alpha\beta}=0$ when $\alpha\neq\beta$.

After the coal granular medium reaches a plastic yield point, according to a plastic potential flow theory, the plastic strain rate tensor is calculated by the law of plastic flow.

$$\dot{\varepsilon}_p^{\alpha\beta} = \dot{\lambda}\frac{\partial Q}{\partial \sigma^{\alpha\beta}} \tag{5}$$

$\dot{\lambda}$ is a non-negative plastic scalar factor, representing the magnitude of a plastic strain increment; $\dot{\lambda}$ is a plastic multiplier; Q is a plastic potential function, which specifies the development direction of plastic strain. According to Eqs. (3) and (5), the total strain rate tensor can be expressed in the form of stress rate.

$$\dot{\varepsilon}^{\alpha\beta} = \frac{\dot{s}^{\alpha\beta}}{2G} + \frac{1-2\upsilon}{3E}\dot{\sigma}^{\gamma\gamma}\delta^{\alpha\beta} + \dot{\lambda}\frac{\partial Q}{\partial \sigma^{\alpha\beta}} \tag{6}$$

According to the standard definition of the total stress tensor, $$\sigma^{\alpha\beta} = s^{\alpha\beta} + \frac{1}{3}\sigma^{\gamma\gamma}\delta^{\alpha\beta},$$

that is, $$\dot{s}^{\alpha\beta} = \dot{\sigma}^{\alpha\beta} - \frac{1}{3}\dot{\sigma}^{\gamma\gamma}\delta^{\alpha\beta}.$$

By substituting the value into Eq. (6) to solve $\dot{\sigma}^{\alpha\beta}$ in reverse, the following incremental stress-strain relationship is obtained:

$$\dot{\sigma}^{\alpha\beta} = 2G\dot{\varepsilon}^{\alpha\beta} + K\dot{\varepsilon}^{\gamma\gamma}\delta^{\alpha\beta} - \dot{\lambda}\left[\left(K-\frac{2G}{3}\right)\frac{\partial Q}{\partial \sigma^{mn}}\delta^{mn}\delta^{\alpha\beta} + 2G\frac{\partial Q}{\partial \sigma^{\alpha\beta}}\right] \tag{7}$$

In the equation, $\dot{e}_{ij} = \dot{\varepsilon}_{ij} - \frac{1}{3}\dot{\varepsilon}_{kk}\delta_{ij}$ represents a partial shear strain rate tensor; m and n are pseudo indexes. On the basis of Eq. (7), a yield criterion is selected to form an equation for the μ(I) rheological constitutive theory.

$$s^{\alpha\beta} = \eta(|\dot{\gamma}|,p)\dot{\gamma}^{\alpha\beta},\ \eta(|\dot{\gamma}|,P) = \mu(I)P/|\dot{\gamma}|,\ I = |\dot{\gamma}|d/(P/\rho_z)^{0.5} \tag{8}$$

Writing Eq. (8) in the form of first and second invariants of the stress tensor leads to:

$$f(I_1,J_2) = \sqrt{J_2} - \mu(I)P = \sqrt{J_2} + \frac{1}{3}\mu(I)I_1 = 0 \tag{9}$$

The plastic flow potential function takes the μ(I) rheological equation (9):

$$Q = \sqrt{J_2} + \frac{1}{3}\mu(I)I_1 = 0 \tag{10}$$

The yield function f also takes Eq. (9), and expands according to the total differential to produce:

$$\frac{\partial f}{\partial \sigma^{\alpha\beta}} = \frac{\partial f}{\partial I_1}\frac{\partial I_1}{\partial \sigma^{\alpha\beta}} + \frac{\partial f}{\partial \sqrt{J_2}}\frac{\partial \sqrt{J_2}}{\partial \sigma^{\alpha\beta}} = \frac{\partial f}{\partial I_1}\delta^{\alpha\beta} + \frac{1}{2\sqrt{J_2}}\frac{\partial f}{\partial \sqrt{J_2}}s^{\alpha\beta} \tag{11}$$

$$\frac{\partial Q}{\partial \sigma^{\alpha\beta}} = \frac{\partial Q}{\partial I_1}\frac{\partial I_1}{\partial \sigma^{\alpha\beta}} + \frac{\partial Q}{\partial \sqrt{J_2}}\frac{\partial \sqrt{J_2}}{\partial \sigma^{\alpha\beta}} = \frac{\partial Q}{\partial I_1}\delta^{\alpha\beta} + \frac{1}{2\sqrt{J_2}}\frac{\partial Q}{\partial \sqrt{J_2}}s^{\alpha\beta} \tag{12}$$

Substituting Eqs. (11) and (12) into Eq. (7) yields a stress-strain relationship under the law of associated plastic flow:

$$\dot{\sigma}^{\alpha\beta} = 2G\dot{\varepsilon}^{\alpha\beta} + K\dot{\varepsilon}^{\gamma\gamma}\delta^{\alpha\beta} - \dot{\lambda}\left[\mu(I)K\delta^{\alpha\beta} + \frac{G}{\sqrt{J_2}}s^{\alpha\beta}\right] \tag{13}$$

Substituting Eq. (7) into a consistency condition equation (14) yields a change rate equation for the plastic flow multiplier in Eq. (13):

$$df = \frac{\partial f}{\partial \sigma^{\alpha\beta}} d\sigma^{\alpha\beta} = 0 \tag{14}$$

That is, the change rate equation of the plastic flow multiplier is:

$$\lambda = \frac{2G\dot{e}^{\alpha\beta}\frac{\partial f}{\partial \sigma^{\alpha\beta}} + \left(K - \frac{2G}{3}\right)\dot{\varepsilon}^{\gamma\gamma}\frac{\partial f}{\partial \sigma^{\alpha\beta}}\delta^{\alpha\beta}}{2G\frac{\partial f}{\partial \sigma^{mn}}\frac{\partial Q}{\partial \sigma^{mn}} + \left(K - \frac{2G}{3}\right)\frac{\partial f}{\partial \sigma^{mn}}\delta^{mn}\frac{\partial g}{\partial \sigma^{mn}}\delta^{mn}} \tag{15}$$

Expressing the plastic potential function in the same form (10) as the yield criterion leads to a change rate equation of the plastic multiplier under the law of associated plastic flow:

$$\lambda = \frac{\mu(I)K\dot{\varepsilon}^{\gamma\gamma} + \left(G/\sqrt{J_2}\right)s^{\alpha\beta}\dot{\varepsilon}^{\alpha\beta}}{\mu^2(I)K + G} \tag{16}$$

To take into account large deformations, the constitutive relationship must adopt a stress rate independent of rigid rotation. In the present disclosure, the Jaumann stress rate $\overset{\triangle}{\sigma}$ is expressed in the following form:

$$\overset{\triangle}{\sigma}^{\alpha\beta} = \dot{\sigma}^{\alpha\beta} - \sigma^{\alpha\gamma}\dot{\omega}^{\beta\gamma} - \sigma^{\beta\gamma}\dot{\omega}^{\alpha\gamma} \tag{17}$$

$\dot{\omega}$ is a spin rate tensor:

$$\dot{\omega}^{\alpha\beta} = \frac{1}{2}\left(\frac{\partial v^{\alpha}}{\partial x^{\beta}} - \frac{\partial v^{\beta}}{\partial x^{\alpha}}\right) \tag{18}$$

Finally, a stress-strain relationship for the visco-elasto-plastic constitutive theory of the dense granular material under the law of associated plastic flow is obtained:

$$\dot{\sigma}^{\alpha\beta} = \sigma^{\alpha\gamma}\dot{\omega}^{\beta\gamma} + \sigma^{\beta\gamma}\dot{\omega}^{\alpha\gamma} + 2G\dot{e}^{\alpha\beta} + K\dot{\varepsilon}^{\gamma\gamma}\delta^{\alpha\beta} - \lambda\left[\mu(I)K\delta^{\alpha\beta} + \frac{G}{\sqrt{J_2}}s^{\alpha\beta}\right] \tag{19}$$

The change rate equation of the plastic multiplier adopts the corresponding law of associated plastic flow in (16). The stress-strain relationship calculated by this equation should always be kept on the yield surface represented by Eq. (9) after the material reaches the yield point. In order to achieve this requirement, the following return principles are adopted:

If the stress state of the material at time step n exceeds the apex of the yield surface, when the following conditions are met:

$$\frac{1}{3}\mu(I)I_1 < 0 \tag{20}$$

the normal stress component is adjusted to a new value so that the hydrostatic pressure corresponds to that at the apex. The adjustment equations are as follows:

$$\sigma_n^{xx} = \sigma_n^{xx} - \frac{1}{3}(I_1^n) \tag{21a}$$

$$\sigma_n^{yy} = \sigma_n^{yy} - \frac{1}{3}(I_1^n) \tag{21b}$$

$$\sigma_n^{zz} = \sigma_n^{zz} - \frac{1}{3}(I_1^n) \tag{21c}$$

In the equations, n represents a moment; the shear stress $\sigma_{xy}^n$, $\sigma_{zz}^n$ and $\sigma_{yz}^n$ remain unchanged.

When an ideal elasto-plastic material undergoes a plastic deformation, the stress state must always be on the yield surface during the plastic loading process, and a stress rescale procedure is used to restore the stress state to the yield surface by introducing a scale factor r. For the μ(I) rheological yield criterion, the scale factor at time step n is defined as:

$$r^n = \frac{-\frac{1}{3}\mu(I)I_1^n}{\sqrt{J_2^n}} \tag{22}$$

Therefore, when the stress state of the dense coal granular medium exceeds the yield surface, according to the μ(I) rheological yield criterion, in correspondence to the following conditions:

$$-\frac{1}{3}\mu(I)I_1^n < \sqrt{J_2^n} \tag{23}$$

the deviation shear stress component decreases according to the scale factor r, while the hydrostatic stress component $I_1$ remains unchanged, according to the following relationship:

$$\sigma_n^{xx} = r^n s_n^{xx} + \frac{1}{3}I_1^n \tag{24a}$$

$$\sigma_n^{yy} = r^n s_n^{yy} + \frac{1}{3}I_1^n \tag{24b}$$

$$\sigma_n^{zz} = r^n s_n^{zz} + \frac{1}{3}I_1^n \tag{24c}$$

$$\sigma_n^{xy} = r^n s_n^{xy} \tag{24d}$$

$$\sigma_n^{xz} = r^n s_n^{xz} \tag{24e}$$

$$\sigma_n^{yz} = r^n s_n^{yz} \tag{24f}$$

Where:

$$I_1^n = \sigma_n^{xx} + \sigma_n^{yy} + \sigma_n^{zz} \tag{25}$$

2) KTGF and Friction Dynamics to Describe the Regime of the Sparse Coal Particle Flow Region ($0.02 \leq \xi_p < 0.5$)
   a: The gas-like regime in the sparse coal particle flow region is described by the KTGF. There are a total of four equations, including a mass conservation equation, a momentum conservation equation, an energy conservation equation and a pseudo-temperature conservation equation:

$$\frac{\partial}{\partial t}(\xi_p \rho_p) + \nabla \cdot (\xi_p \rho_p v_p) = 0 \quad (26)$$

$$\frac{\partial}{\partial t}(\xi_p \rho_p v_p) + \nabla \cdot (\xi_p \rho_p v_p v_p) - \nabla P_p + \nabla \cdot \tau_p + \xi_p \rho_p f \quad (27)$$

$$\frac{3}{2}\left[\frac{\partial}{\partial t}(\rho_p \xi_p \theta_p) + \nabla \cdot (\rho_p \xi_p v_p \theta_p)\right] = \quad (29)$$

$$(-P_p I + \tau_p) : \nabla v_p + \nabla \cdot (k_p \nabla \theta_p) - N_c \theta_p$$

The subscript p represents the coal granular medium; &$\xi_p$, $\rho_p$ and $v_p$ represent the volume fraction, density and velocity of the coal granular medium respectively; $\nabla P_p$ represents a pressure gradient of the coal granular medium; $\xi_p \rho_p f$ represents the other external force on the coal granular medium. In the present disclosure, the force mainly refers to gravity. $h_p$ represents an energy enthalpy of the coal granular medium; $q_p$ represents the quantity of heat transfer inside the coal granular medium. $\tau_p$ represents a viscous stress tensor of the coal granular medium.

$$\tau_p = \xi_p \mu_p (\nabla v_p + \nabla v_p^T) + \xi_p \left(\lambda_p - \frac{2}{3}\mu_p\right)\nabla \cdot v_p I \quad (30)$$

$\mu_p$ and $\lambda_p$ represent a shear viscosity and a bulk viscosity of the coal granular medium respectively; I represents a unit tensor. The description of the pressure $P_p$ and viscous stress $\tau_p$ of the coal granular medium is introduced to realize the closure of the control equations (27) and (28) of the coal granular medium. According to the KTGF, the particle phase pressure $P_p$ and viscous stress $\tau_p$ are related to the maximum value of the particle velocity fluctuation, and the particle velocity fluctuation is described by the particle pseudo-temperature. The pseudo-temperature conservation equation of the particle is Eq. (29), where $(-p_p I + \tau_p):\nabla v_p$ represents energy generated by the corresponding force of the particle, $k_p \nabla \theta_p$ represents an energy dissipation term, $k_p$ represents an energy dissipation coefficient, and $N_c \theta_p$ represents an energy dissipation term generated by the collision between particles. The specific equation is:

$$k_p = \quad (31)$$

$$2\xi_p^2 \rho_p d_p g_0 (1+e_{pp}) \sqrt{\frac{\theta_p}{\pi}} + \frac{2\frac{75\sqrt{\pi}}{384}\rho_p d_p \sqrt{\theta_p}}{g_0(1+e_{pp})}\left(1+\frac{6}{5}\xi_p g_0(1+e)\right)^2$$

$$N_c \theta_p = 3(1-e^2)\xi_p^2 \rho_p g_0 \theta_p \left[\frac{4}{d_p}\sqrt{\frac{\theta_p}{\pi}} - \nabla \cdot v_p\right] \quad (32)$$

$$P_p = \xi_p \rho_p [1 + 2(1+e)\xi_p g_0]\theta_p \quad (33)$$

$$\tau_p = \zeta_p \nabla \cdot v_p I + 2\mu_p S = \frac{4\xi_p^2 \rho_p d_p g_0 (1+e_{pp})}{3}\sqrt{\frac{\theta_p}{\pi}}\nabla \cdot v_p I + 2 \quad (34)$$

$$\frac{4\xi_p^2 \rho_p d_p g_0 (1+e_{pp})}{5}\sqrt{\frac{\theta_p}{\pi}} + \frac{2\frac{5\sqrt{\pi}}{96}\rho_p d_p \sqrt{\theta_p}}{g_0(1+e_{pp})}\left(1+\frac{4}{5}\xi_p g_0(1+e_{pp})\right)^2$$

In the equations, $d_p$ represents a diameter of the coal particle; $e_{pp}$ represents a collision coefficient of restitution (COR) between coal particles; $\xi_p$ represents an effective bulk viscosity of the particle phase produced by particle collisions, which is an intermediate variable; $g_0$ represents a radial COR of the particle:

$$g_0 = \left[1 - \left(\frac{\xi_p}{\xi_{p,max}}\right)^{\frac{1}{3}}\right]^{-1} \quad (35)$$

$\xi_{p,max}$ represents the maximum volume fraction that the coal granular medium can reach under compressible conditions.

b: The transitional regime between the liquid-like and gas-like regimes in the sparse coal particle flow region is described by a combination of KTGF and friction dynamics. The normal stress and shear stress of the particle phase can be written as follows:

$$p_p = \begin{cases} p_{KTGF} + p_{friction} & \xi_p > \xi_{p,min} \\ p_{KTGF} & \alpha_p > \alpha_{p,min} \end{cases} \quad (36)$$

$$\mu_p = \begin{cases} \mu_{KTGF} + \mu_{friction} & \xi_p > \xi_{p,min} \\ \mu_{KTGF} & \alpha_p > \alpha_{p,min} \end{cases} \quad (37)$$

In the equations, $P_{KTGF}$ and $P_{friction}$ represent a KTGF part and a friction part of the coal particle pressure $P_p$ respectively; $\mu_{KTGF}$ and $\mu_{friction}$ represent a KTGF part and a friction part of the shear viscosity $\mu_p$ of the coal particle respectively; $\xi_{p,min}$ represents the volume fraction of the particle when the friction stress starts to gradually increase. According to the available data, no friction behavior between particles is observed when it is less than $\xi_{p,max}$. Therefore, it is assumed that when the uniformly distributed particles are no longer in contact, the frictional interaction no longer occurs, and the mutual stress is mainly generated by the collision. The normal stress of the coal particles caused by friction is expressed by a semi-empirical model proposed by Johnson et al.:

$$p_{friction} = Fr \frac{(\xi_p - \xi_{p,min})^a}{(\xi_{p,max} - \xi_p)^b} \quad (38)$$

In the equation, Fr, a and b are empirical constants of the material. For glass beads, the empirical values of $\xi_{p,min}$, Fr, a and b are respectively 0.5, 0.05, 2.0 and 5.0. Regarding the calculation of the friction viscosity, Schaeffer first derived the following relationship between the friction shear stress and the normal stress by assuming that the ideal rigid-plastic constitutive theory was obeyed in the process of studying the flow of a granular material from a silo through a tapered outlet under gravity:

$$\Xi^{\alpha\beta} = p\sqrt{2}\sin\phi|\dot{\gamma}|^{-1}\dot{\gamma}^{\alpha\beta} \quad (39)$$

$$\mu_{friction} = p\sqrt{2}\sin\phi \quad (40)$$

$\tau^{\alpha\beta}$ represents a shear stress, p represents a normal stress, $\phi$ represents an internal friction angle, $\dot{\gamma}^{\alpha\beta}$ represents a strain rate tensor, $|\dot{\gamma}|$ represents a 2-norm $|\dot{\gamma}|=(0.5\dot{\gamma}^{\alpha\beta}\dot{\gamma}^{\alpha\beta})^{0.5}$ of $\dot{\gamma}^{\alpha\beta}$, and the total stress $\sigma^{\alpha\beta}=-P\delta^{\alpha\beta}+\tau^{\alpha\beta}$. Johnson et al. also proposed a similar equation between the frictional shear force and the normal stress that obeys the Coulomb's law. The in-depth analysis of Eq. (40) shows that this equation has the same form as the μ(I) rheological shear force calculation equation, but the difference lies in the shear force coefficient. The shear force coefficient is $\sqrt{2}\sin\phi$ in the friction dynamics equation and $\mu(I)=\mu_s+(\mu_2-\mu_s)/(I_0/I+1)$ in the rheological equation, which changes from $\mu_s$ to $\mu_2$. It is even more surprising to find through experiments that in the friction dynamics equation, the internal friction angle $\phi$ is 28.5 for glass beads, while in the rheological equation, the typical values for glass beads are $\mu_s=\tan(21°)$, $\mu_2=\tan(33°)$, which means that $\sqrt{2}\sin\phi\approx\mu_2$. This indicates that friction dynamics is the limit of the $\mu(I)$ rheological equation when the inertial parameter or shear strain rate is infinite.

3) Particle Dynamics to Describe the Regime of the Ultra-Sparse Coal Particle Flow Region When the characteristic time scale of the macroscopic flow of coal particles is significantly smaller than that of the microscopic collision, the macroscopic continuum description of the gas-like regime of coal particles is no longer valid. In other words, when the volume fraction of the coal particle phase is less than a certain value, the two-body collision assumption between coal particles is no longer satisfied. At this time, it is necessary to introduce the theory of particle dynamics to describe the movement and collision of microscopic single particles. This regime is defined as an ultra-sparse coal particle flow regime, or an inertial regime, in which particles mainly perform inertial motion, supplemented by collisions between particles.

Particle dynamics refers to the dynamic process of describing objects with certain mass but negligible geometric dimensions by Newton's three laws. Based on Newton's second law, an equation of the relationship between the acceleration of a particle and the force is established, which is the basic model of particle dynamics. When the particle is subjected to n forces $F_i$ (i=1, 2, ..., n), the equation is $$m\frac{d^2r}{dt^2} = m\ddot{r} = \sum_{i=1}^{n} F_i \quad (41)$$

In the equation, r represents a radius vector of the particle, and the superscript "..." represents a second derivative with respect to time. Eq. (41) is a differential equation in vector form, also known as the basic equation of particle dynamics. When analyzing and calculating actual problems, the basic equation can be expressed as a set of differential equations in corresponding forms according to different coordinate systems for application.

The $F_i$ in the right side is determined according to the actual force of the particle, such as inertial force, gravity, buoyant force, electrostatic force, liquid bridge force, inter-particle collision force, gas-particle drag force, particle wall collision force, molecular bond force and van der Waals force. In the present disclosure, the inertial force, drag, gravity, buoyant force and pressure-gradient force experienced by the particles during movement are considered.

The inertial force experienced by coal particles during movement is:

$$F_{inertia} = -\frac{1}{6}\pi d_p^2 \rho_p \frac{dv_p}{dt} \quad (42)$$

In the actual two-phase flow, the drag of coal particles is affected by many factors. It is not only related to the Reynolds number $Re_p$ of the particles, but also related to the turbulent motion of the fluid, the compressibility of the fluid, the temperature of the fluid, the temperature and shape of the particle, the existence of the wall surface and the concentration of the particle group. Therefore, the drag of coal particles is difficult to express in a unified form. For research convenience, the concept of drag coefficient is introduced, which is defined as:

$$C_D = \frac{F_r}{\pi r_p^2 \left[\frac{1}{2}\rho(v-v_p)^2\right]} \quad (43)$$

Thus, the drag of the particles can be expressed as:

$$F_{drag} = \frac{\pi r_p^2}{2} C_D \rho |v-v_p|(v-v_p) \quad (44)$$

In the equation, $r_p^2$ represents a radius of spherical coal particles, $\rho$ represents a fluid density, and v represents a fluid velocity.

The gravity of the particles is:

$$F_g = \frac{1}{6}\pi d_p^2 \rho_p g \quad (45)$$

The buoyant force exerted on the particles by external air is:

$$F_b = \frac{1}{6}\pi d_p^2 g \quad (46)$$

When particles move in a flow field with a pressure gradient, they will also be subjected to a force caused by the pressure gradient. The pressure gradient force is expressed as:

$$F_p = -V_p \frac{\partial P}{\partial x} \quad (47)$$

In the equation, $V_p$ represents the volume of coal particles, and the negative sign indicates that the direction of the pressure gradient force is opposite to the direction of the pressure gradient in the flow field. Generally speaking, the pressure gradient force is small in magnitude compared with the inertial force, and thus can be ignored.

4) Transformation Principle Between the Dense Coal Particle Flow and the Sparse Coal Particle Flow The liquid-like and gas-like regimes are effectively coupled by adding a transitional regime there-between. The transitional regime is described by a combination of the KTGF and friction dynamics. The friction dynamics is mainly used for an assumption that the particles are in long-term contact and the friction stress is dominant in the calculation of the liquid-like or solid-like regime. Some scholars have demonstrated through research that although friction dynamics can be used in the simulation of high volume fractions, there is uncertainty in the calculation of the regime at higher volume fractions. By introducing the visco-elasto-plastic constitutive theory of the dense coal particle flow, the defects of friction dynamics are completely overcome. Meanwhile, the phenomenological advantages of the method is effectively combined, and the stress in this regime can be effectively calculated with a simple equation while the physical mechanism cannot be fully clarified. Therefore, it is necessary to maintain the conservation of the force at the interface between the liquid-like and transitional regimes during the transformation process. On the one hand, the regime is transformed by setting the volume fraction to transform. On the other hand, when the transformation is set, the normal stress calculated by the constitutive calculation of the dense coal particle flow is the same as the normal stress calculated by the friction dynamics, and the shear stress calculated by the constitutive calculation of the dense coal particle flow is the same as the shear stress calculated by the friction dynamics. The normal stress is the identical, namely:

$$p_e = p_{friction} = Fr \frac{(\xi_p - \xi_{p,min})^a}{(\xi_{p,max} - \xi_p)^b} \quad (48)$$

In the above equation, $a, b, \xi_{p,min}, \xi_{p,max}$ are fixed values, and Fr is calculated from the identical normal stress when the two regimes are transformed into each other. This guarantees the conservation of energy during the transformation of the two regimes and the rationality of the value of Fr.

The shear stress remains the same. The in-depth analysis of Eq. (40) shows that this equation has the same form as the $\mu(I)$ rheological shear force calculation equation, but the difference lies in the shear force coefficient. The shear force coefficient is $\sqrt{2} \sin \phi$ in the friction dynamics equation and $\mu(I) = \mu_s + (\mu_2 - \mu_s)/(I_0/I+1)$ in the rheological equation, which changes from $\mu_s$ to $\mu_2$. It is even more surprising to find through experiments that in the friction dynamics equation, the internal friction angle is 28.5 for glass beads, while in the rheological equation, the typical values for glass beads are $u_s = \tan(21°)$, $\mu_2 = \tan(33°)$, which means that $\sqrt{2} \sin \phi \approx \mu_2$. This indicates that friction dynamics is the limit of the $\mu(I)$ rheological equation when the inertial parameter or shear strain rate is infinite. Therefore, in the calculation of the shear stress, $\mu(I)$ is directly used instead of $\sqrt{2} \sin \phi$ in the friction dynamics, which more guarantees the conservation and rationality of the calculation. Of course, with the set transformation volume fraction and the inertial parameter under this condition, $\mu(I)$ basically tends to the maximum $\mu_2$, which is basically the same as $\sqrt{2} \sin \phi$ in the friction dynamics.

Starting from point B of the transformation from the liquid-like regime to the transitional regime, the KTGF calculation begins. The pseudo-temperature $\theta_p$ of the particles is accumulated from zero, and the collision effect between the particles gradually comes into play. At point C, the friction between the particles disappears completely, completely transformed into the collision between particles, and a gas-like regime starts.

According to the above calculation process of the transitional regime, the transitional regime established in this way can effectively connect the liquid-like and gas-like regimes to achieve the purpose of smooth transition, while fully complying with the laws of physics.

5) Transformation Principle Between the Sparse Coal Particle Flow and the Ultra-Sparse Coal Particle Flow When the particle volume fraction is small to a certain value ($\leq 2\%$), the characteristic time scale of the macroscopic flow of particles is obviously smaller than that of the microscopic collision, and the macroscopic continuum description of the gas-like regime of the particles is no longer valid. Then it turns to tracking the particles. In the gas-like calculation process, a macroscopic pseudo-fluid assumption is proposed. A unit represents the statistical average information of the particle at that position in space, including the effective density, the mean particle size and the mean velocity of the particle. Therefore, in the of transformation process, it is necessary to ensure the conservation of the mass, momentum and energy. The discrete solution of the sparse coal particle flow adopts a Lagrangian particle method, and the simulation of the particle dynamics of the ultra-sparse coal particle flow also adopts a particle method. In this way, the transformation process is natural, and ensures the conservation of the physical quantities. Meanwhile, in order to be closer to reality, a particle splitting algorithm may also be combined to make the two corresponding in space.

Step 104: Numerically discretize the constitutive theoretical model by using a numerical method to obtain discrete equations.

1) SPH Method to Describe the Regime of the Dense Coal Particle Flow Region

First, discretizing the visco-elasto-plastic theoretical model equations (1) of the dense coal particle flow by using the SPH method leads to:

$$\frac{d\rho_i}{dt} = \sum_{j=1}^{N} m_j (v_i^\alpha - v_j^\alpha) \cdot \frac{\partial W_{ij}}{\partial x^\alpha} \quad (49a)$$

$$\frac{dv_i^\alpha}{dt} = \sum_{j=1}^{N} m_j \left( \frac{\sigma_i^{\alpha\beta}}{\rho_i^2} + \frac{\sigma_j^{\alpha\beta}}{\rho_j^2} \right) \frac{\partial W_{ij}}{\partial x^\beta} + f^\alpha \quad (49b)$$

$$\frac{dx_i^\alpha}{dt} = v_i^\alpha \quad (49c)$$

In the equations, i,j represent particle i and particle j respectively; $W_{ij}$ represent a value of a kernel function between particle i and particle j; W represents the kernel function; h represents a smooth length.

The total stress tensor equation (19) also requires the use of the SPH method for discretization, and the total stress tensor of each particle needs to be calculated:

$$\frac{d\sigma_i^{\alpha\beta}}{dt} = \quad (50)$$

$$\sigma_i^{\alpha\gamma}\omega_i^{\beta\gamma} + \sigma_i^{\beta\gamma}\omega_i^{\alpha\gamma} + 2G\dot{e}_i^{\alpha\beta} + K\dot{\varepsilon}_i^{\gamma\gamma}\delta_i^{\alpha\beta} - \dot{\lambda}_i \left[ \mu(I) K \delta_i^{\alpha\beta} + \frac{G}{\sqrt{J_2}} s_i^{\alpha\beta} \right]$$

The plastic multiplier $\dot{\lambda}_i$ of particle i is still in the form of Eq. (51) after the SPH discretization:

$$\dot{\lambda}_i = \frac{\mu_i(I) K_i \dot{\varepsilon}_i^{\gamma\gamma} + (G/\sqrt{J_2}) s^{\alpha\beta} \dot{\varepsilon}^{\alpha\beta}}{\mu_i^2(I) K_i + G_i} \quad (51)$$

The strain rate and rotational strain rate tensor in Eqs. (50) and (51) also need SPH discretization:

$$\dot{\varepsilon}_i^{\alpha\beta} = \quad (52)$$

$$\frac{1}{2}\left(\frac{\partial v^\alpha}{\partial x^\beta} + \frac{\partial v^\beta}{\partial x^\alpha}\right) = \frac{1}{2}\left[\sum_{j=1}^{N}\frac{m_j}{\rho_j}(v_j^\alpha - v_i^\alpha)\frac{\partial W_{ij}}{\partial x_i^\beta} + \sum_{j=1}^{N}\frac{m_j}{\rho_j}(v_j^\beta - v_i^\beta)\frac{\partial W_{ij}}{\partial x_i^\alpha}\right]$$

$$\dot{\omega}_i^{\alpha\beta} = \quad (53)$$

$$\frac{1}{2}\left(\frac{\partial v^\alpha}{\partial x^\beta} + \frac{\partial v^\beta}{\partial x^\alpha}\right) = \frac{1}{2}\left[\sum_{j=1}^{N}\frac{m_j}{\rho_j}(v_j^\alpha - v_i^\alpha)\frac{\partial W_{ij}}{\partial x_i^\beta} + \sum_{j=1}^{N}\frac{m_j}{\rho_j}(v_j^\beta - v_i^\beta)\frac{\partial W_{ij}}{\partial x_i^\alpha}\right]$$

After the variations dρ and dv$^\alpha$ of density ρ and velocity v$^\alpha$ are obtained by Eqs. (49), the physical quantities at a new moment are updated according to the following equation:

$$\varphi_i(t+\delta t/2)=\varphi_i(t-\delta t/2)+d\varphi_i(t)\delta t \tag{51}$$

$$x_i^\alpha(t+\delta t)=x_i^\alpha(t)+v_i^\alpha(t+\delta t/2)\delta t \tag{52}$$

In the equations, $\varphi_i$ represents the density ρ and velocity v$^\alpha$ of particle i; $x_i^\alpha$ represents the position coordinates of particle i in direction α; $d\varphi_i(t)$ represents $dv_i^\alpha(t)$ and $d\rho_i(t)$ calculated by Eqs. (49); δt represents an initial constant time step.

2) SDPH Method to Describe the Regime of the Sparse Coal Particle Flow Region

Discretizing the control equations (27), (28) and (29) of the sparse coal granular medium region by using the SDPH method leads to:

$$\frac{d\rho_i}{dt}=\sum_{j=1}^{N}m_j(v_i^\alpha-v_j^\alpha)\cdot\frac{\partial W_{ij}}{\partial x^\alpha} \tag{54}$$

$$\frac{dv_i^\alpha}{dt}=\sum_{j=1}^{N}m_j\left(\frac{\sigma_i^{\alpha\beta}}{\rho_i^2}+\frac{\sigma_j^{\alpha\beta}}{\rho_j^2}+\prod_{ij}\right)\frac{\partial W_{ij}}{\partial x^\beta}+f^\alpha \tag{55}$$

$$\frac{d\theta_{pi}}{dt}=\frac{2}{3}\left(\frac{1}{2}\sum_{j=1}^{N}m_j v_{ji}\left(\frac{\sigma_i^{\alpha\beta}}{\rho_i^2}+\frac{\sigma_j^{\alpha\beta}}{\rho_j^2}-\prod_{ij}\right)\frac{\partial W_{ij}}{\partial x^\beta}+\right. \tag{56}$$

$$\left.\sum_{j=1}^{N}m_j\left(\frac{k_p(\nabla\theta_p)_i^{\alpha\beta}}{\rho_i^2}+\frac{k_p(\nabla\theta_p)_j^{\alpha\beta}}{\rho_j^2}\right)\frac{\partial W_{ij}}{\partial x^\beta}-N_c\theta_{pi}\right)$$

$\Pi_{ij}$ represents an artificial viscosity between particle i and particle j, which is calculated by the following equation:

$$\prod_{ij}=-\frac{\alpha\bar{h}_{ij}c_s}{\bar{\rho}_{ij}}\frac{(v_i^\alpha-v_j^\alpha)\cdot(r_i^\alpha-r_j^\alpha)}{r_{ij}^2+\varepsilon\bar{h}_{ij}^2} \tag{57}$$

In the equation, $$\bar{h}_{ij}=\frac{h_i+h_j}{2}, \bar{\rho}_{ij}=\frac{\rho_i+\rho_j}{2};$$

ε=0.01, which is used to prevent the numerical divergence generated when the particles are close to each other. The constant α is generally set to 1 for simulating shock waves. In the present disclosure, when simulating the coal granular medium, the minimum α is 0.02 to ensure stable calculation.

In the SDPH method, the mass of SDPH particles is equal to the total mass of the particle group they represent; the density of SDPH particles is the effective density of the particle group; the velocity of SDPH particles is the mean velocity of the particle group; the pseudo-temperature and pressure are the mean pseudo-temperature and mean pressure of the represented particle group. In addition, SDPH particles carry the mean particle size, variance and number of single particles that characterize the particle size distribution of the particle group.

The SPH discretization equation of the pseudo-temperature gradient is:

$$(\nabla\theta_p)_i^\alpha=m_i\sum_{j=1}^{N}\frac{\theta_{pj}-\theta_{pi}}{\rho_{ij}}\frac{\partial W_{ij}}{\partial x^\alpha} \tag{58}$$

The particle phase pressure and shear force equations involved in closing the above equations are Eqs. (30) to (34).

After the variations dρ, dv$^\alpha$ and $d\theta_p$ of density ρ, velocity v$^\alpha$ and pseudo-temperature $\theta_p$ are obtained by Eqs. (54) to (56), the physical quantities at a new moment are updated according to the following equations:

$$\varphi_i(t+\delta t/2)=\varphi_i(t-\delta t/2)+d\varphi_i(t)\delta t \tag{59}$$

$$x_i^\alpha(t+\delta t)=x_i^\alpha(t)+v_i^\alpha(t-\delta t/2)\delta \tag{60}$$

In the equations, $\varphi_i$ represents the density ρ, velocity v$^\alpha$ and pseudo-temperature $\theta_p$ of particle i; $x_i^\alpha$ represents the position coordinates of particle i in direction α; $d\varphi_i(t)$ represents $d\rho_i(t)$, $dv_i^\alpha(t)$ and $d\theta_p$ calculated by Eqs. (54) to (56); δt represents an initial constant time step.

3) DEM Method to Describe the Regime of the Ultra-Sparse Coal Particle Flow Region Discretizing the differential equation (41) describing the regime of the ultra-sparse coal particle flow region by using the DEM method leads to:

$$m_i\frac{dv_i^\alpha}{dt}=\sum_{j=1}^{k_i}(F_{c,ij}^\alpha+F_{d,ij}^\alpha)+m_i f^\alpha \tag{61}$$

In the equation, $m_i$ and $v_i^\alpha$ represent the mass and velocity of coal particle i respectively; t represents time; $m_i f^\alpha$ represents the external force received by the particle; $F_{c,ij}^\alpha$ and $F_{d,ij}^\alpha$ represent a contact force and a viscous contact damping force of coal particles i and j respectively; $k_i$ represents the total number of particles in contact with the coal particles.

The contact force $F_{c,ij}^\alpha$ between particles i and j is decomposed into a normal contact force and a tangential contact force, namely:

$$F_{c,ij}^\alpha=F_{cn,ij}^\alpha=F_{ct,ij}^\alpha \tag{62}$$

The normal contact force is calculated by a Hertz model:

$$F_{cn,ij}^\alpha=-\frac{4}{3}E^*\sqrt{R^*}\delta_n^{3/2}n^\alpha \tag{63}$$

Where:

$$E^*=\frac{E}{2(1-\nu^2)}, R^*=\frac{1}{R_i}+\frac{1}{R_j} \tag{64}$$

$\delta_n$ represents a penetration depth when coal particles i and j are in contact:

$$\delta_n=R_i+R_j-|R_j-R_i| \tag{65}$$

The tangential contact force is calculated by a Coulomb criterion:

$$|F_{ct,ij}|=\begin{cases}|F_{ct,ij}|, & |F_{ct,ij}|<\mu_z|F_{cn,ij}|\\ \mu_z|F_{cn,ij}|, & |F_{ct,ij}|\geq\mu_z|F_{cn,ij}|\end{cases} \tag{66}$$

In the equation, $\mu_i$ represents a coefficient of static friction, and the direction of the tangential friction is opposite to the trend of relative slipping.

The viscous contact damping force $F_{d,ij}^\alpha$ is also decomposed into normal and tangential components, namely:

$$F_{d,ij}^\alpha = F_{dn,ij}^\alpha + F_{dt,ij}^\alpha \quad (67)$$

The normal viscous contact damping force $F_{dn,ij}^\alpha$ is calculated as follows:

$$F_{dn,ij}^\alpha = -c_n(v_{ij}^\alpha \cdot n^\alpha)n^\alpha \quad (68)$$

In the equation, $c_n$ represents a normal viscous contact damping coefficient.

The tangential contact damping force $F_{dt,ij}^\alpha$ is calculated as follows:

$$F_{dt,ij}^\alpha = c_t(v_{ij} \times n) \times n \quad (69)$$

In the equation, $c_t$ represents a tangential viscous contact damping coefficient.

After the above force parameters are obtained, the equation of motion is solved to obtain the time-dependent variation of velocity $dv_i^\alpha$. According to Eqs. (51) and (52), the velocity and the particle position at a new moment are calculated by using a leapfrog update method.

4) Transformation and Interaction Between the SPH Algorithm for the Dense Coal Particle Flow and the SDPH Algorithm for the Sparse Coal Particle Flow a. Transformation Between the SPH Algorithm for the Dense Coal Particle Flow and the SDPH Algorithm for the Sparse Coal Particle Flow The SPH algorithm for the dense coal particle flow and the SDPH algorithm for the sparse coal particle flow are the same in characterizing the properties of particles. These two algorithms both carry traditional parameters such as the mass, velocity, position and pressure of the particles, as well as the particle size distribution and volume fraction of the particles. The SDPH algorithm also carries particle properties such as the pseudo-temperature introduced by the KTGF. The calculation framework of SPH and SDPH is the same, except that the SPH discretizes the visco-elasto-plastic constitutive model of the dense coal particle flow, while the SDPH discretizes the KTGF constitutive model of the sparse coal particle flow. The transformation between the SPH algorithm of the dense coal particle flow and the SDPH algorithm of the sparse coal particle flow is mainly controlled by the volume fraction of particles, and the volume fraction of particles is mainly determined by the effective density of the particles, that is, the SPH or SDPH density. The equation is as follows:

$$\alpha_p = \frac{\hat{\rho}_p}{\rho_p} \quad (70)$$

$\alpha_p$ represents the volume fraction of coal particles, $\hat{\rho}_p$ represents the effective density of coal particles, which is the density of the SPH or SDPH particles, and $\rho_p$ represents the actual density of particles. The calculation $\hat{\rho}_p$ of follows the law of conservation of mass.

$$\text{method} = \begin{cases} SPH & \alpha_p \geq \alpha_{critical} \\ SDPH & \alpha_p < \alpha_{critical} \end{cases} \quad (71)$$

Principles of transformation from SPH to SDPH:

First, the physical parameters of coal particles, such as the position, velocity, density and energy are kept unchanged. The main difference lies in the interaction between particles. The SPH normal stress of the dense coal particle flow is calculated by the law of elasticity, and the shear stress is calculated by summing the elastic shear stress and plastic shear stress. The two forces should also remain unchanged during the transformation to SDPH, that is, the SPH elastic normal stress should be transformed into an SDPH friction normal stress:

$$p_e = p_{friction} = Fr\frac{(\alpha_z - \alpha_{z,min})^n}{(\alpha_{z,max} - \alpha_z)^m} \quad (72)$$

The reverse calculation of Eq. (72) yields Fr as an invariant, and then the value of the normal stress generated by friction is updated according to the change of the volume fraction $\alpha_z$. For the friction shear stress, $\tau = \mu(I)p|\dot{\gamma}|/\dot{\gamma}$ is continuously calculated by using the $\mu(I)$ rheological shear stress equation, but at this time p starts to be calculated by Eq. (72). The elastic shear stress caused by long-term contact is set to zero. The above demonstrates the SDPH calculation of the normal stress and shear stress generated in the transitional region by friction dynamics, which ensures the conservation of the transformed momentum. Meanwhile, starting from the transformation, the SDPH pseudo-temperature is calculated from zero, so that the normal stress and shear stress generated by the collisions gradually increase, until the calculation of the transitional region is completely transformed into that by the KTGF model.

Principles for transformation from SDPH to SPH:

Similarly, first, the physical parameters of particles, including the position, velocity, density and energy are kept unchanged. The main difference lies in the interaction between particles. The SDPH pseudo-temperature gradually decreases in the reverse direction from the transitional region, and the stress caused by the mutual collision gradually decreases. The normal friction stress $p_{friction}$ gradually increases, and the friction shear stress also increases. The calculation is performed by the rheological shear stress equation, and the value of Fr is that determined by the previous calculation until a transformation point begins, and the regimes changes from gas-like to liquid-like. At this time, it is ensured that the value of the elastic normal stress in the liquid-like regime is equal to the value of the friction normal stress, and the value of the plastic flow shear stress continues to be calculated according to the rheological shear stress equation. As the shear force gradually decreases, the elastic shear force gradually increases, the particle velocity gradually decreases, and the volume fraction gradually increases. According to the law of plastic flow, the unloading process of the coal granular medium material is calculated until it returns to a static state. Because the particles have undergone a flow process, the coal granular medium cannot be restored to its original state and is in a quasi-static state in another position and regime.

b. Interaction Between the SPH Algorithm for the Dense Coal Particle Flow and the SDPH Algorithm for the Sparse Coal Particle Flow When the dense coal particle flow and the sparse coal particle flow coexist, there is an interaction between the particles in the two flow regimes, and there is also an interaction between the SPH particles and SDPH particles in calculation. Both SPH and SDPH calculations rely on neighboring particle search. Therefore, when SPH particles and SDPH particles are used as neighboring particles, it is necessary to determine whether the two are involved in the calculation of each other. First, SDPH particles are taken as active particles and SPH particles as passive particles. When the SDPH method calculates the normal stress and shear stress between particles by assuming the two-body collision, the particles in the dense coal particle flow regime produce a stress similar to the two-body collision on the particles in the sparse coal particle flow regime. As long as one of two interacting particles is in a sparse regime, it can be considered that the two particles are also within the assumed range of two-body collision. Therefore, SPH particles contribute to SDPH particles, and participate in the calculation of the velocity gradient of SDPH particles. When SPH particles are taken as active particles, the calculation of the dense coal particle flow mainly depends on the ideal elasto-viscoplastic constitutive model of long-term contact. When SDPH particles are taken as neighboring particles of SPH particles, since the SDPH distance between the particles exceeds the long-term contact range, SDPH particles cannot provide a force of long-term contact with SPH particles, and do not participate in the calculation of the velocity gradient of SPH particles. In addition, the normal stress and shear stress calculated by the SDPH particles and the total stress calculated by the SPH particles participate in each other's calculation.

5) Transformation and Interaction Between the SDPH Algorithm for the Sparse Coal Particle Flow and the DEM Algorithm for the Ultra-Sparse Coal Particle Flow a. Transformation Between the SDPH Algorithm for the Sparse Coal Particle Flow and the DEM Algorithm for the Ultra-Sparse Coal Particle Flow When the volume fraction of SDPH particles in the sparse coal particle flow drops to a certain threshold (<0.02), it no longer follows the KTGF model of the two-body collision assumption, so the SDPH particles are transformed into DEM particles for calculation. The transformation strategy is to transform one SDPH particle into one DEM particle. The parameters of the SDPH particles, such as the mass, velocity, stiffness and position are the same as those of the DEM particles after transformation. The density of the DEM particles is the density of the actual particles. Therefore, the size of the DEM particles after transformation can be calculated according to the mass and density thereof:

$$m_{SDPH} = m_{DEM} \tag{73a}$$

$$v_{SDPH} = v_{DEM} \tag{73b}$$

$$x_{SDPH} = x_{DEM} \tag{73c}$$

$$\rho_{DEM} = \rho_{particle} \tag{73d}$$

$$r_{DEM} = \sqrt[3]{\frac{3}{4} \frac{m_{DEM}}{\pi \rho_{DEM}}} \tag{73e}$$

The DEM particles transformed by this method actually represent a particle group, and the specific number of particles in the particle group is the same as that of the SDPH particles. This method is equivalent to converging these number of actual particles to the center of mass of the current DEM particles. The density is the same as the actual particle density, and the size is equal to the size of these particles after they are gathered together. There is a certain deviation from reality. However, as the size of the entire coal particle flow is large and the number of DEM particles is small, it is reasonable to approximate the discrete phase instead of solving it. While the amount of calculation does not increase, the fidelity of the physical model is improved.

b. Interaction Between the SDPH Algorithm for the Sparse Coal Particle Flow and the DEM Algorithm for the Ultra-Sparse Coal Particle Flow The interaction between the DEM particles and SPH particles or SDPH particles in ultra-sparse particle simulation is calculated by the law of interaction between DEM particles. According to the method of transforming SDPH particles into DEM particles, SDPH particles are transformed into DEM particles invisibly. Then the interaction force between SDPH and DEM particles (equivalent to two DEM particles) is calculated, including a contact force $F_{c,ij}=F_{cn,ij}+F_{ct,ij}$ and a normal contact damping force $F_{d,ij}=F_{dn,ij}+F_{dt,ij}$. The forces acting between SDPH and DEM particles are equal in magnitude and opposite in direction, and are added to the calculation of respective equations as a source term of the momentum equation:

SDPH momentum equation considering the effect of DEM particles on SDPH particles:

$$\frac{dv_{i,SDPH}^{\alpha}}{dt} = \sum_{j=1}^{N} m_j \left( \frac{\sigma_i^{\alpha\beta}}{\rho_i^2} + \frac{\sigma_j^{\alpha\beta}}{\rho_j^2} \right) \frac{\partial W_{ij}}{\partial x^{\beta}} + g^{\alpha} + F_{DEM}^{\alpha} \tag{74}$$

DEM momentum equation considering the effect of SDPH particles on DEM particle:

$$m_i \frac{dv_{i,DEM}}{dt} = \sum_{j=1}^{k_i} (F_{c,ij} + F_{d,ij}) + m_i g + F_{SDPH} \tag{75}$$

$F_{DEM}^{\alpha}$ represents a component of the force of DEM particles acting on SDPH particles in direction $\alpha$, and $F_{SDPH}$ represents a vector of the force of DEM particles acting on SDPH particles.

After the establishment of the all-flow-regime numerical method for the coal granular medium, the conservation equation's discrete equations (49), (54) to (56) and (59) obtained in Step (3) and the leapfrog time update equations (51) and (52) are written by using the C++ program. The transformation and interaction between the different algorithms are implemented by using the method described in Step (3). After the writing of the program, the Microsoft Visual Studio2017 compiler is used to compile to realize the calculation of the program.

Step 105: Calculate a movement process of the coal granular medium according to the discrete equations and the particle model of the coal granular medium to obtain a calculation result, where the calculation result includes a field variable and a displacement. Specifically:

Step 1051: Set an initial velocity of the coal granular medium to 0 and an initial pseudo-temperature to 0, and determine an initial position of the coal granular medium according to the particle model of the coal granular medium. Before Step 1051, the parameters of the coal granular medium material are selected, including the diameter of coal particles 0.32 mm, the actual density 2,600 kg/m³, the initial volume fraction 0.6, the bulk density 1,560 kg/m³, the elastic modulus 20 GPa, the Poisson's ratio 0.3 and the internal friction angle 30°. The SPH method is used for initial discretization with the following parameters: the density of SPH particles (the effective density of particles) 1,560 kg/m³, the initial volume fraction 0.6, the diameter of SPH particles 5 mm and the smooth length 6.5 mm. The total number of particles varies according to different working conditions. The boundary force calculation method of the potential function is used to determine the boundary condition of the coal granular medium.

Step 1052: Calculate a variation of the field variable per unit time and a variation of the displacement per unit time at each time step starting from moment 0 by the discrete equations.

Step 1053: Perform leapfrog time update according to the variation of the field variable per unit time and the variation of the displacement per unit time to determine the field variable and displacement at all moments.

After completing the settings according to Steps 1051-1052, the variations $d\rho$, $dv$ and $d\theta_p$ of field variables $\rho$, $v$ and $\theta_p$ per unit time and the variation $dx$ of displacement $x$ per unit time at each time step starting from moment 0 are calculated by the written program in the computer. Then leapfrog time update is performed to obtain field variables $\rho$, $v$, $\theta_p$ and displacement $x$ at the next moment. Thus, the field variables of the coal granular medium at all moments are obtained (Step 1053), that is, the whole-process dynamic data of the movement of the coal granular medium.

Step 106: Plot the calculation result by using post-processing software Tecplot to obtain relevant information of a coal particle flow, where the relevant information includes a spatial distribution, a velocity field distribution, a spreading range and accumulation height information of the coal particle flow.

The data obtained in Step 105 are imported into Tecplot to generate an image of the distribution of the coal granular medium material in space at each moment, which displays the velocity vector, flow regime index, shear strain, etc. specific particles in the model are selected as the research object. The change data of the particles' related parameters over time are extracted, and a time history curve of the particles' related variables is generated through Tecplot.

The calculation results of the new model and method are analyzed and demonstrated below with reference to two typical examples.

Figure 7:
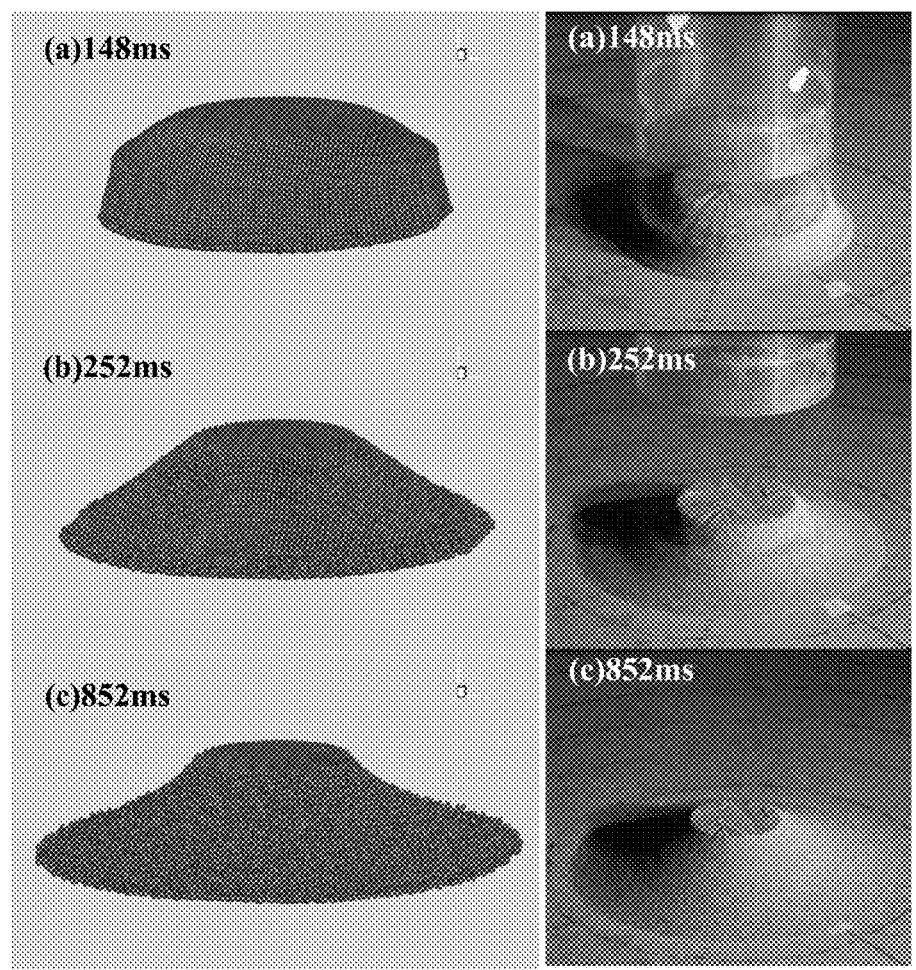
FIG. 7 shows a comparison between calculation results of the new method of the present disclosure and experimental results, both regarding the movement and final deposition form of a coal granular medium in a three-dimensional (3D) particle cylinder (length-to-diameter ratio 0.55) at different moments.

FIG. 7 shows a comparison between calculation results of the new method of the present disclosure and experimental results, both regarding the movement and final deposition form of a coal granular medium in a 3D particle cylinder (length-to-diameter ratio 0.55) at different moments. It can be seen that the calculation results and the experimental results are in good agreement in terms of deposition profile, the flow regime distribution of the coal granular medium, the collapse and spreading range of particles and the accumulation height, which verifies the effectiveness of the present disclosure in calculating all flow regimes of the coal granular medium.

Figure 8:
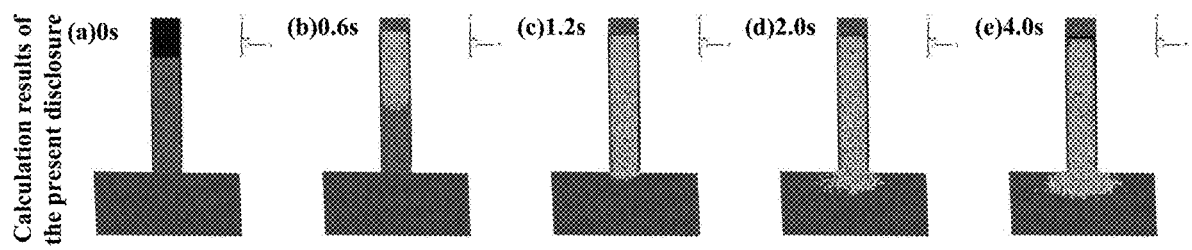
FIG. 8 shows calculation results of a process of coal particles slipping along a chute according to the present disclosure.

FIG. 8 shows calculation results of a process of coal particles slipping along a chute according to the present disclosure. This figure shows the detailed process of the coal particles gradually collapsing and moving downward along the wall of the chute after the release of the baffle. The calculation results well capture the movement form, velocity vector distribution, accumulation process and accumulation form of the coal granular medium. The finally obtained particle spreading range is in good agreement with that shown by the experimental results, which again verifies that the new method of the present disclosure is suitable for the numerical simulation of the all-flow-regime process of the coal granular medium.

Step 107: Determine whether the pulverized coal transportation process is safe according to the relevant information of the coal particle flow. Specifically:

Step 1071: Obtain historical data on slippage of the pulverized coal.

Step 1072: Obtain a threshold of safety-related parameters of the pulverized coal transportation process according to the historical data on slippage of the pulverized coal, where the safety-related parameters of the pulverized coal transportation process includes the spatial distribution, the velocity field distribution, the spreading range and the accumulation height information of the coal particle flow.

Step 1073: Determine whether the spatial distribution, the velocity field distribution, the spreading range and the accumulation height information of the coal particle flow are greater than the respective threshold.

Step 1074: Determine that the pulverized coal transportation process is not safe, that is, the coal particles will slip, if the safety-related parameters of the pulverized coal transportation process are greater than the respective threshold.

Step 1075: Determine that the pulverized coal transportation process is safe if the safety-related parameters of the pulverized coal transportation process are not greater than the respective threshold.

The present disclosure analyzes the internal stress change process, yield flow process, rapid flow process and accumulation process of the coal granular medium, and reveals the movement mechanism of particles in different flow regimes and the interaction mechanism between different flow regimes. The present disclosure provides support for explaining the complex movement phenomenon of the coal granular medium material and for establishing theoretical prediction models. In addition, the present disclosure can accurately and quickly determine whether the pulverized coal transportation process is safe, and determine the range of movement and spreading after the pulverized coal slips down based on the spatial distribution, velocity field distribution, spreading range and accumulation height information of the coal particle flow. The present disclosure can guide relevant personnel to take precautions before the pulverized coal slips, or to provide effective rescue in the actual damaged area after the pulverized coal slips.

Figure 9:
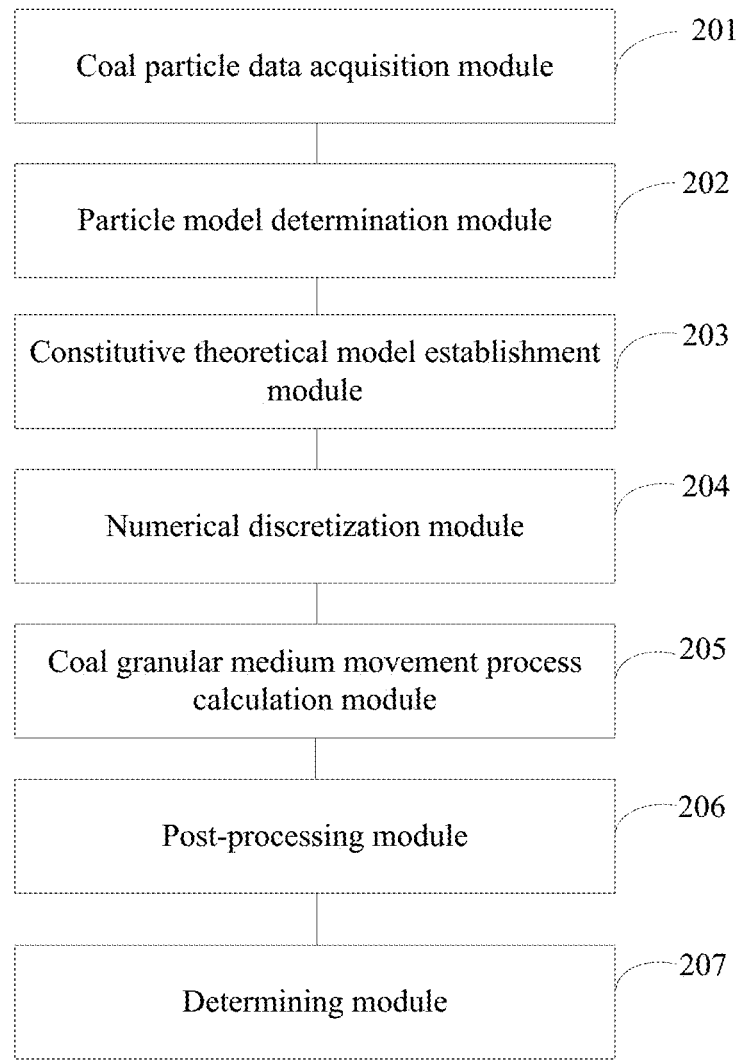
FIG. 9 is a structural diagram of a system for determining transportation safety of pulverized coal according to the present disclosure.

As shown in FIG. 9, the present disclosure provides a system for determining transportation safety of pulverized coal. The system includes a coal particle data acquisition module, a particle model determination module, a constitutive theoretical model establishment module, a numerical discretization module, a coal granular medium movement process calculation module, a post-processing module and a determining module.

The coal particle data acquisition module 201 is used for acquiring coal particle data during transportation of pulverized coal, where the coal particle data is the size data of a coal particle accumulation, including length data, width data and height data of the coal particle accumulation.

The particle model determination module 202 is used for determining a particle model of the coal granular medium during the transportation of the pulverized coal according to the size data.

The constitutive theoretical model establishment module 203 is used for establishing a constitutive theoretical model to describe all flow regimes of a coal granular medium, where the all flow regimes of the coal granular medium include solid-like, liquid-like, gas-like and inertial regimes.

The numerical discretization module 204 is used for numerically discretizing the constitutive theoretical model by using a numerical method to obtain discrete equations.

The coal granular medium movement process calculation module 205 is used for calculating a movement process of the coal granular medium according to the discrete equations and the particle model of the coal granular medium to obtain a calculation result, where the calculation result includes a field variable and a displacement.

The post-processing module 206 is used for plotting the calculation result by using post-processing software Tecplot to obtain relevant information of a coal particle flow, where the relevant information includes a spatial distribution, a velocity field distribution, a spreading range and accumulation height information of the coal particle flow.

The determining module 207 is used for determining whether the pulverized coal transportation process is safe according to the relevant information of the coal particle flow.

The particle model determination module 202 specifically includes:
  a 3D geometric model establishment unit, for determining a 3D geometric model of the coal particle during the transportation of the pulverized coal according to the size data; and
  a meshing unit, for meshing the 3D geometric model by using meshing software to obtain a particle model.

The constitutive theoretical model establishment module 203 specifically includes:
  a sparseness-based defining module, for defining solid-like and liquid-like particles as a dense coal particle flow, gas-like particles as a sparse coal particle flow and inertial particles as an ultra-sparse coal particle flow according to different levels of sparseness;
  a theoretical model establishment unit, for establishing a theoretical model to describe a dense coal particle flow region, a theoretical model to describe a sparse coal particle flow region and a theoretical model to describe an ultra-sparse coal particle flow region respectively; and
  a transformation principle establishment unit, for establishing a principle of transformation between the dense coal particle flow and the sparse coal particle flow and a principle of transformation between the sparse coal particle flow and the ultra-sparse coal particle flow respectively.

The coal granular medium movement process calculation module 205 specifically includes:
  an initial condition setting unit, for setting an initial velocity of the coal granular medium to 0 and an initial pseudo-temperature to 0, and determining an initial position of the coal granular medium according to the particle model of the coal granular medium;
  a first determination unit, for calculating a variation of the field variable per unit time and a variation of the displacement per unit time at each time step starting from moment 0 by the discrete equations; and
  a second determination unit, for performing leapfrog time update according to the variation of the field variable per unit time and the variation of the displacement per unit time to determine the field variable and displacement at all moments.

The present disclosure realizes the description of all flow regimes of the coal granular medium. The present disclosure can effectively describe the coal granular medium's static solid-like regime, yielding liquid-like regime, fast gas-like regime and ultra-sparse inertial regime. The present disclosure overcomes the shortcomings of traditional technologies that only describe a single flow regime or only superimpose several regimes. The present disclosure defines and describes the theories of the coal granular medium in different flow regimes, and gives a specific description of the transformation methods and principles between different flow regimes, which has good practicability and strong operability. The present disclosure is more suitable for the numerical simulation of the actual coal particle flow in nature and industrial engineering, and effectively explains the typical phenomena existing in the coexistence and transformation process of the multiple flow regimes of the coal granular medium.

The present disclosure has a small amount of calculation and occupies less calculation resources. The multi-flow-regime theory of the coal granular medium established by the present disclosure is a theory based on the law of macroscopic continuum mechanics. Except that the inertial regime of the particles does not comply with the assumption of continuum mechanics, the other three flow regimes all follow this assumption, which solves the heavy calculation burden brought by the traditional molecular dynamics theory or mesoscopic discrete element theory for the single-regime description of the coal granular medium. Meanwhile, the present disclosure establishes a suitable multi-method coupled technique based on these theories. The present disclosure adopts the most suitable numerical method to discretize each regime, for example, the SPH numerical simulation method for the solid-like and liquid-like regimes, the SDPH numerical simulation method for the gas-like regime and the DEM simulation method for the inertial regime. The simulations of the particles before reaching the inertial regime are based on Lagrangian particle hydrodynamics. Compared with the traditional DEM method, the present disclosure reduces the calculation amount by about 10 times. Since the proportion of particles reaching the inertial regime is very small, the inertial regime of particles is calculated by DEM, and the amount of calculation increased by the use of this method is very limited. In addition, compared with the traditional MPM, the present disclosure simulates the multiple flow regimes of the coal granular medium without the need to establish a background mesh or to repeatedly interpolate between the particle and the mesh, thereby reducing the complexity and the amount of calculation.

Each embodiment of the specification is described in a progressive manner. Each embodiment focuses on the difference from other embodiments, and the same and similar parts between the embodiments may refer to each other. For a system disclosed in the embodiments, since the system corresponds to the method disclosed in the embodiments, the description is simple, and reference may be made to the method description.

In this specification, several specific embodiments are used for illustration of the principles and implementations of the present disclosure. The description of the foregoing embodiments is used to help illustrate the method of the present disclosure and the core ideas thereof. In addition, those of ordinary skill in the art can make various modifications in terms of specific implementations and scope of application in accordance with the ideas of the present disclosure. In conclusion, the content of this specification should not be construed as a limitation to the present disclosure.

What is claimed is:

1. A method for determining transportation safety of pulverized coal, comprising:
  acquiring coal particle data during transportation of pulverized coal, wherein the coal particle data is the size data of a coal particle accumulation, comprising length data, width data and height data of the coal particle accumulation;

determining a particle model of the coal particle accumulation during the transportation of the pulverized coal according to the size data;

establishing a constitutive theoretical model to describe all flow regimes of a coal granular medium, wherein the all flow regimes of the coal granular medium comprise solid-like, liquid-like, gas-like and inertial regimes;

numerically discretizing the constitutive theoretical model by using a numerical method to obtain discrete equations;

calculating a movement process of the coal granular medium according to the discrete equations and the particle model of the coal granular medium to obtain a calculation result, wherein the calculation result comprises a field variable and a displacement;

plotting the calculation result by using post-processing software Tecplot to obtain relevant information of a coal particle flow, wherein the relevant information comprises a spatial distribution, a velocity field distribution, a spreading range and accumulation height information of the coal particle flow; and determining whether the pulverized coal transportation process is safe according to the relevant information of the coal particle flow;

wherein the determining whether the pulverized coal transportation process is safe according to the relevant information of the coal particle flow specifically comprises:

obtaining historical data on slippage of the pulverized coal;

obtaining a threshold of safety-related parameters of the pulverized coal transportation process according to the historical data on slippage of the pulverized coal, wherein the safety-related parameters of the pulverized coal transportation process comprise the spatial distribution, the velocity field distribution, the spreading range and the accumulation height information of the coal particle flow;

determining whether the spatial distribution, the velocity field distribution, the spreading range and the accumulation height information of the coal particle flow are greater than the respective threshold;

determining that the pulverized coal transportation process is not safe if the safety-related parameters of the pulverized coal transportation process are greater than the respective threshold; and determining that the pulverized coal transportation process is safe if the safety-related parameters of the pulverized coal transportation process are not greater than the respective threshold.

2. The method for determining transportation safety of pulverized coal according to claim 1, wherein the determining a particle model of the coal particle accumulation during the transportation of the pulverized coal according to the size data specifically comprises:

determining a three-dimensional (3D) geometric model of the coal particle accumulation during the transportation of the pulverized coal according to the size data; and meshing the 3D geometric model by using meshing software to obtain a particle model.

3. The method for determining transportation safety of pulverized coal according to claim 1, wherein the establishing a constitutive theoretical model to describe all flow regimes of a coal granular medium specifically comprises:

defining solid-like and liquid-like particles as a dense coal particle flow, gas-like particles as a sparse coal particle flow and inertial particles as an ultra-sparse coal particle flow according to different levels of sparseness;

establishing a theoretical model to describe a dense coal particle flow region, a theoretical model to describe a sparse coal particle flow region and a theoretical model to describe an ultra-sparse coal particle flow region respectively; and establishing a principle of transformation between the dense coal particle flow and the sparse coal particle flow and a principle of transformation between the sparse coal particle flow and the ultra-sparse coal particle flow respectively.

4. The method for determining transportation safety of pulverized coal according to claim 1, wherein the calculating a movement process of the coal granular medium according to the discrete equations and the particle model of the coal granular medium to obtain a calculation result specifically comprises:

setting an initial velocity of the coal granular medium to 0 and an initial pseudo-temperature to 0, and determining an initial position of the coal granular medium according to the particle model of the coal granular medium;

calculating a variation of the field variable per unit time and a variation of the displacement per unit time at each time step starting from moment 0 by the discrete equations; and performing leapfrog time update according to the variation of the field variable per unit time and the variation of the displacement per unit time to determine the field variable and displacement at all moments.

\* \* \* \* \*